United States Patent
Gregg

(10) Patent No.: US 11,135,200 B2
(45) Date of Patent: Oct. 5, 2021

(54) ANTIMICROBIAL DRUG SYNTHESIS AND THERAPEUTIC COMPOSITIONS

(71) Applicant: John Malcolm Hall Gregg, Princeton, NJ (US)

(72) Inventor: John Malcolm Hall Gregg, Princeton, NJ (US)

(\*) Notice: Subject to any disclaimer, the term of this patent is extended or adjusted under 35 U.S.C. 154(b) by 0 days.

(21) Appl. No.: 16/885,585

(22) Filed: May 28, 2020

(65) Prior Publication Data
US 2020/0360344 A1    Nov. 19, 2020

Related U.S. Application Data

(63) Continuation of application No. 15/973,939, filed on May 8, 2018, now abandoned, which is a continuation of application No. 14/967,542, filed on Dec. 14, 2015, now abandoned.

(60) Provisional application No. 62/124,467, filed on Dec. 20, 2014, provisional application No. 62/124,468, filed on Dec. 20, 2014, provisional application No. 62/124,469, filed on Dec. 20, 2014, provisional application No. 62/124,470, filed on Dec. 20, 2014, provisional application No. 62/124,471, filed on Dec. 20, 2014, provisional application No. 62/124,472, filed on Dec. 20, 2014.

(51) Int. Cl.
| | |
|---|---|
| A61K 31/4164 | (2006.01) |
| C07D 233/94 | (2006.01) |
| A61K 45/06 | (2006.01) |
| A61K 9/00 | (2006.01) |

(52) U.S. Cl.
CPC ........ *A61K 31/4164* (2013.01); *A61K 9/0014* (2013.01); *A61K 45/06* (2013.01); *C07D 233/94* (2013.01); *Y02A 50/30* (2018.01)

(58) Field of Classification Search
CPC .. A61K 31/4164; A61K 9/0014; A61K 45/06; C07D 233/94; A61P 31/00; Y02A 50/30
See application file for complete search history.

(56) References Cited

U.S. PATENT DOCUMENTS

| | | | |
|---|---|---|---|
| 8,647,676 B2 | 2/2014 | Nygaard et al. | |
| 2008/0177083 A1 | 7/2008 | Wang et al. | |
| 2011/0111017 A1 | 5/2011 | Bosio et al. | |
| 2013/0202698 A1* | 8/2013 | Wang | A61K 9/0019 424/465 |
| 2015/0224177 A1* | 8/2015 | Bordeau | A61K 31/185 424/667 |

FOREIGN PATENT DOCUMENTS

| | | | |
|---|---|---|---|
| CN | 1695596 A | 11/2005 | |
| CN | 102641267 A | 8/2012 | |
| CN | 103751131 A | 4/2014 | |
| CN | 104013618 A | 9/2014 | |
| EP | 1875910 A1 * | 1/2008 | ............ A61K 47/10 |
| EP | 1875910 A1 | 1/2008 | |
| WO | 2000025756 A2 | 5/2000 | |
| WO | 2012123774 A1 | 9/2012 | |

OTHER PUBLICATIONS

Gursoy et. al., J. Periodontal., publ. 2010, vol. 81, pp. 1081-1091 (Year: 2010).*
Hamad et. al., Antimicrob. Agents & Chemother., publ. Jul. 2011, vol. 55(7), pp. 3313-3323 (Year: 2011).*
Hu et. al., Int. J. Antimicrobial Agents, publ. Jul. 29, 2014, vol. 44, pp. 514-519 (Year: 2014).*
Kim et. al., Plos One, , publ. May 2011, vol. 6(5), e19867, pp. 1-14 (Year: 2011).*
Mills et. al., Clinical Evidence, publ. 2011, vol. 04, pp. 1-38 (Year: 2011).*
Chao et. al., Nutrition Rev., publ. 2012, vol. 70(7), pp. 373-386 (Year: 2012).*
Currenti, Cell Mol. Neurobiol., publ. 2010, vol. 30, pp. 161-171 (Year: 2010).*
Hartgrinket. al., Lancet, publ. 2009, vol. 374, pp. 477-490 (Year: 2009).*
Le Hello et. al., Emerging Infec. Dis., publ. 2005, vol. 11(10), 1607-1609 (Year: 2005).*
Stewart et. al., Emerging Infec. Dis., publ. 2011, vol. 17(7), pp. 1286-1288 (Year: 2011).*
Larsen, J.C. et al., "Pathogenesis of Burkholderia pseudomallei and Burkholderia mallei", Military Medicine, vol. 174, p. 647-651, Jun. 2009.
B. Currie, Melioidosis: The 2014 Revised RDH Guideline, The Northern Territory Disease Control Bulletin, vol. 21, No. 2, pp. 4-8, Jun. 2014.
Sullivan, R.P. et al., "2020 Review and revision of the 2015 Darwin melioidosis treatment guideline; paradigm drift, not shift", PLOS—Neglected Tropical Diseases, pp. 1-13, Sep. 28, 2020.
Chao et al, Nutrition Rev., 2012, 70(7), pp. 373-386.
Currenti, Cell Mol Neurobia, 2010, 30, 161-171.
Goronek L. et al "The diagnosis and tretment of Clostridium difficile in antibiotic-associated diarrhea", 199, Hepatogastroenterology, 1999, 46(25), pp. 343-348.

(Continued)

*Primary Examiner* — Sarah Pihonak
(74) *Attorney, Agent, or Firm* — Anthony D. Sabatelli; Wiggin and Dana LLP

(57) ABSTRACT

This invention relates to the medical use of an antimicrobial agent, racemic Ornidazole, its (R) and (S) enantiomers, or pharmaceutically acceptable salts or esters thereof, and to methods of treatment which involve treating a subject with Ornidazole. The racemic (rac)-ornidazole, its enantiomers, or pharmaceutically acceptable salts or esters thereof, may be used in combination with other actives. The invention also relates to pharmaceutical formulations and compositions comprising (rac)-ornidazole, (R)-ornidazole, (S)-ornidazole, or pharmaceutically acceptable salts or esters thereof, and/or other actives as well as methods to stereoselectively manufacture the enantiomers.

7 Claims, 1 Drawing Sheet

(56) References Cited

OTHER PUBLICATIONS

Gursoy et al., J. Periodontal., 2010, 81, 1081-1091.
Hamad et al., Antimicrob. Agents & Chemother., 2011, 55(7), pp. 3313-3323.
Hartgrink et al., Lancet, 2009, 374, pp. 477-490.
Hu et al., Int. J. Antimicrobial Agents, 2014, 44, pp. 514-519.
Huang et al. "Chiral Separation of rac-Ornidazole and detection of the impurity or (R)-Ornidazole injection and raw material." Chirality 18.8 (2006): 587-591).
Jarmuda S. et al. "Potential role of demodex mites and bacteria in the induction of rosacea", 2012, Journal of Medical microbiology, 2012, 61, pp. 1504-1510, abstract.
Kim et al., Plos One, 2011, 6(5), e19867, pp. 1-14.
Larsen, J.C., et al. "pathogenesis of Burkholderia pseudomallei and Burkholderia mallei", 2009, Military Medicine, 174, 6, pp. 647-651.
Mills et al. "Clinical Evidence", 2011, 4, pp. 1-38.
Wendel, K. et al. "Trichomoniasis: Challenges to Appropriate Management", Clin Infect Dis, 2007, 44 (supplement 3), pp. S123-S129, p. S123, col. 1.
International Search Report and Written Opinion dated Apr. 28, 2016 from Application No. PCT/US2015/065545, 8 pages.
International Preliminary Report on Patentability dated Jun. 20, 2017 from Application No. PCT/US2015/065545, 6 pages.

\* cited by examiner

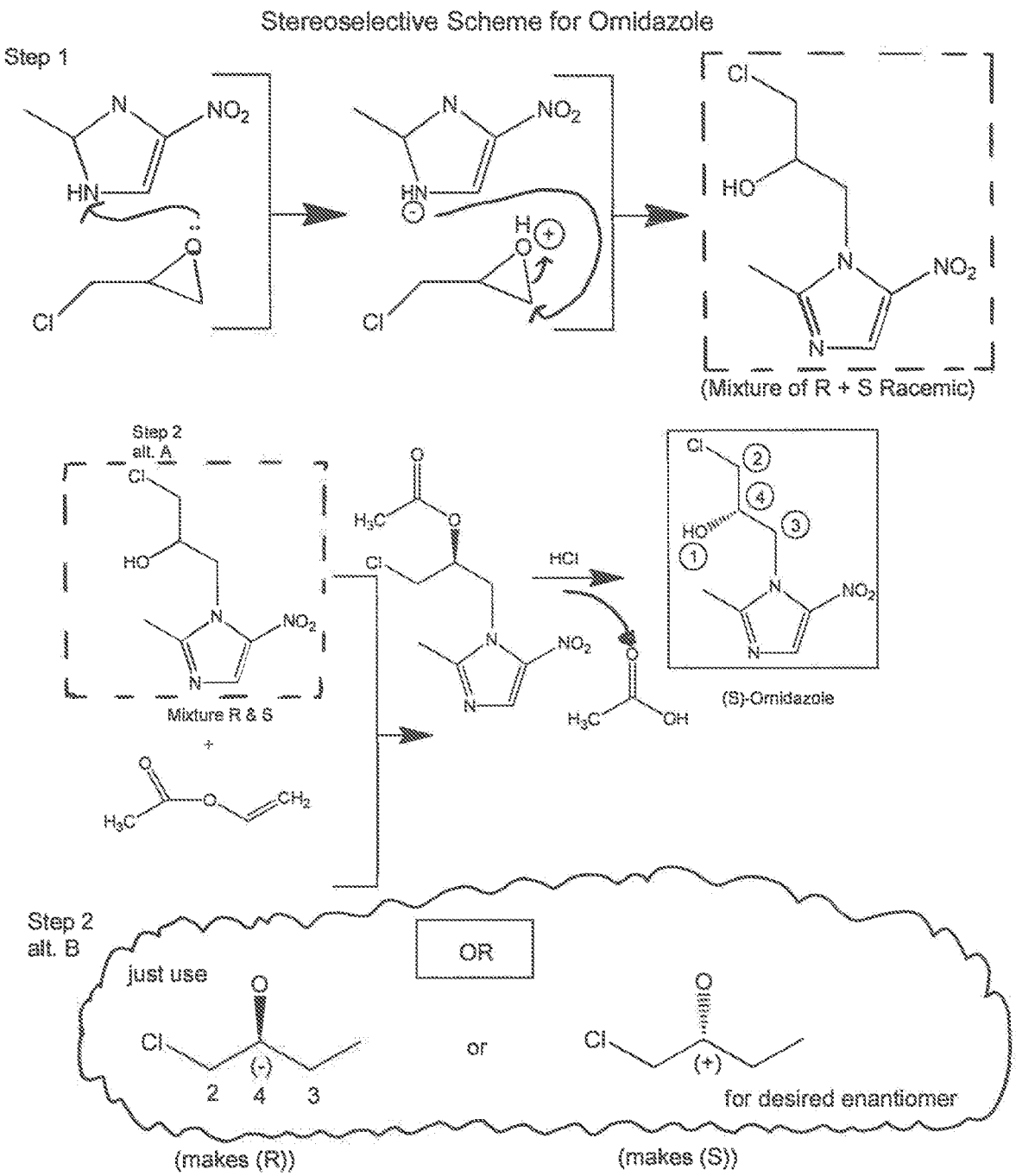

ANTIMICROBIAL DRUG SYNTHESIS AND THERAPEUTIC COMPOSITIONS

CROSS-REFERENCE TO RELATED APPLICATIONS

This application is a continuation of U.S. Nonprovisional application Ser. No. 15/973,939, filed May 8, 2018, which is a continuation of U.S. Nonprovisional application Ser. No. 14/967,542, filed Dec. 14, 2015, which claims the benefit of: U.S. Provisional Application Ser. No. 62/124,467, filed Dec. 20, 2014; U.S. Provisional Application Ser. No. 62/124,468, filed Dec. 20, 2014, U.S. Provisional Application Ser. No. 62/124,469, filed Dec. 20, 2014, U.S. Provisional Application Ser. No. 62/124,470, filed Dec. 20, 2014, U.S. Provisional Application Ser. No. 62/124,471, filed Dec. 20, 2014, U.S. Provisional Application Ser. No. 62/124,472, filed Dec. 20, 2014, all of which are incorporated herein by reference in their entireties.

BACKGROUND

ORNIDAZOLE is a nitroimidazole anti-infective. Its systematic (IUPAC) name is 1-chloro-3-(2-methyl-5-nitro-1H-imidazol-1-yl)propan-2-ol and its chemical formula is $C_7H_{10}ClN_3O_3$. Ornidazole contains a single chiral centre and thus exists as either the S-enantiomer or the R-enantiomer.

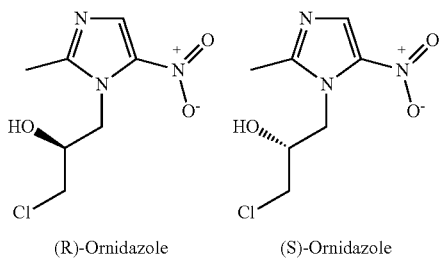

(R)-Ornidazole  (S)-Ornidazole

Both the (R)-ornidazole enantiomer (hereinafter referred to as, "(R)-ornidazole"), and the (S)-ornidazole enantiomer (hereinafter referred to as, "(S)-ornidazole") have both different and unique individual spectrums of activity as well as pharmacological & safety advantages over racemic ornidazole (rac)-ornidazole). (R)-ornidazole, (S)-ornidazole, and (rac)-ornidazole are new chemical entities (NCEs) in the United States and have not been marketed in this jurisdiction or cleared by the Food & Drug Administration (FDA).

The beneficial properties of (R)-ornidazole, (S)-ornidazole, and (rac)-ornidazole include a favorable pharmacokinetic and pharmacodynamic profile and high degree of susceptibility to pathogenic strains of bacteria when the right (minimum inhibitory or bacteriocidal) drug concentrations are employed at the site of infections. In addition, (R)-ornidazole, (S)-ornidazole, and (rac)-ornidazole are effective at treating and eradicating bacterial biofilms of many pathogens that have sensitivity in their planktonic forms at lower MICs than the biofilm form. Many bacterial species are inducible facultative morphologs. An inducible facultative morpholog species can reversibly change configuration from planktonic to biofilm forms and morphological intermediates (such as round body/cystic/and spore forms) based on environmental conditions and through quorem sensing mediated by chemical signalling.

These inducible morphologies, e.g., biofilms and their intermediate forms, have MICs that can be orders of magnitude higher than the planktonic forms of the bacteria. The lethal dose of the antibiotics for bacteria in the biofilm form is called the "minimal bacterial eradication concentration" or "MBEC". The ability ability of the bacteria to shift into a biofilm form serves as an antimicrobial resistance (AMR) mechanism for usually administered dosages of antimicrobials.

(R)-ornidazole, (S)-ornidazole, and (rac)-ornidazole are highly effective in treating biofilms bacterial configurations that these bacteria utilize to combat therapeutics and maintain recurrence reservoirs. The microorganisms in biofilms live in a self-produced matrix of hydrated extracellular polymeric substances (EPS) that form their immediate environment. EPS are mainly polysaccharides, proteins, nucleic acids and lipids; they provide the mechanical stability of biofilms, mediate their adhesion to surfaces and form a cohesive, three-dimensional polymer network that interconnects and transiently immobilizes biofilm cells. In addition, the biofilm matrix acts as an external digestive system by keeping extracellular enzymes close to the cells, enabling them to metabolize dissolved, colloidal and solid biopolymers.

Planktonic isolates are susceptible to common antibiotics. Strains in biofilms and anaerobic configurations are markedly resistant to many antimicrobial agents. However, many of these biofilms and perisistor cells within the biofilm are sensitive to (R)-ornidazole, (S)-ornidazole, and (rac)-ornidazole when exposed to a MBEC and when used in combination with monosaccharides and oligosaccharides that increase the metabolic activity of the cells within the biofilm increasing antimicrobial uptake and toxicity.

Thus, the use of (R)-ornidazole, (S)-ornidazole, and (rac)-ornidazole may provide a number of advantages including, for example, formulations targeting the site of infections or dysbiosis/bacterial overgrowth in biofilms or formulations utilizing smaller amounts of the active drug than alternative treatments, so that patients can ingest smaller tablets or capsules, or allowing the (R)-ornidazole, (S)-ornidazole, and (rac)-ornidazole to be combined with other active agent(s) in a single unit dosage form; allowing more convenient dosing schedules and increasing patient compliance. For example, (R)-ornidazole, (S)-ornidazole, and (rac)-ornidazole are rapidly absorbed after oral administration and have a longer terminal elimination half-life (approximately 14-18 hours) than commonly used drugs in the imidazole class. Accordingly these drugs may be administered less frequently and/or at a lower dose, thus improving patient compliance while providing a therapeutically effective treatment of an infection.

Additionally, (R)-ornidazole, (S)-ornidazole, and (rac)-ornidazole are more active than metronidazole, another nitro-imidazole used therapeutically, for many anaerobic and aerobic bacterial strains (including both Gram positive and Gram negative strains). Even against strains in which (R)-ornidazole, (S)-ornidazole, and (rac)-ornidazole are as active, or even less active than metronidazole, they still offers other benefits.

(R)-ornidazole, (S)-ornidazole, and (rac)-ornidazole are active against both susceptible and resistant strains of anaerobic or aerobic, Gram negative or Gram positive bacteria. Resistant strains of a specific bacteria are strains of that bacteria which are resistant to one or more drugs normally used to treat bacterial infections, e.g. strains of bacteria which are resistant to metronidazole.

For many bacterial strains and parasitic protozoal organisms (R)-ornidazole and (S)-ornidazole are more active than (rac)-ornidazole. Likewise, for many bacterial strains and parasitic protozoal organisms, (R)-ornidazole and (S)-ornidazole are more active than (rac)-Ornidazole.

(R)-ornidazole, (S)-ornidazole, and (rac)-ornidazole also confers certain specific efficacy and safety benefits. For example Ornidazole appears to be free of inductive and inhibitory activity against CYP enzymes know to cause drug-drug interaction problems, does not have a disulfirmam like interaction with alcohol that has been associated with other nitro-imidazoles, and is not a carcinogen.

SUMMARY OF THE INVENTION

The present invention relates to methods of treating and/or reducing the incidence of various diseases by administering to a subject in need thereof a therapeutically effective amount of (R)-ornidazole, (S)-ornidazole, and (rac)-ornidazole, or pharmaceutically acceptable salts or esters thereof. In some embodiments, (R)-ornidazole and (S)-ornidazole, or pharmaceutically acceptable salts or esters thereof, have an enantiomeric purity of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), at least about 95% enantiomeric excess (ee), at least about 96% enantiomeric excess (ee), at least about 97% enantiomeric excess (ee), at least about 98% enantiomeric excess (ee), or at least about 99% enantiomeric excess (ee).

The methods of the present invention also include treating a disease associated with a gastrointestinal, abdominal or intra-abdominal infection; the method comprising administering to a subject in need thereof a therapeutically effective amount of (R)-ornidazole, (S)-ornidazole, and (rac)-ornidazole, or pharmaceutically acceptable salts or esters thereof. In many cases, the therapeutically effective amount of (R)-ornidazole, (S)-ornidazole, and (rac)-ornidazole, or pharmaceutically acceptable salts or esters thereof, for treating the planktonic form of relevant bacteria is lower than the amount necessary to achieve a higher concentration that is the MBEC for a biofilm of that bacteria. Anotherwords, the microbiological breakpoints are different and a totally different dosing strategy is needed based on the assessment of the MBEC rather than the in-vitro planktonic MIC. In this context, when discussing the therapeutically effective amount of (R)-ornidazole, (S)-ornidazole, and (rac)-ornidazole, it is meant the amount necessary to treat and kill the bacteria within the biofilm, not merely the planktonic bacteria, and this may sometimes require the co-administration of an oligosaccarharide or monosaccharide to increase the metabolism of the bacteria within the biofilm to make (R)-ornidazole, (S)-ornidazole, and (rac)-ornidazole more effective.

In a specific embodiment, the diseases treated by (R)-ornidazole, (S)-ornidazole, and (rac)-ornidazole are caused by a bacterial infection.

Another embodiment of the invention includes a method of treating a disease associated with a gastrointestinal, abdominal or intra-abdominal infection; the method comprising administering to a subject in need thereof a therapeutically effective amount of (R)-ornidazole, (S)-ornidazole, and (rac)-ornidazole, or pharmaceutically acceptable salts or esters thereof.

In another specific embodiment, the disease is one or more diseases selected from the group consisting of complicated and uncomplicated diverticulitis, psuedomembranous colitis, biofilms of toxigenic *C. difficile* infection including *C. difficile* which are sporulating and in a spore or hard round-body morphological configuration, or a biofilm configuration that may be more resistant to concentrations of bacteria determined in vitro assessing the planktonic form of the bacteria, infectious/*Clostridium difficile*-associated diarrhea including those which are toxigenic strains of *C. difficile* which are sporulating and in a spore or hard round-body morphological configuration and biofilm configuration that may be more resistant to concentrations of bacteria determined in vitro assessing the planktonic form of the bacteria, cholangitis, cholecystitis, pancreatitis, peritonitis, intra-abdominal/bowel/pelvic/liver abscess (non-protozoal in origin), ulcerative colitis, chronic gastritis, gastric cancer, colorectal cancer, ulcerative colitis, peptic ulcers, gastroduadenal ulcers, and Crohn's Disease.

Thus, the disease that may be treated by (R)-ornidazole, (S)-ornidazole, and (rac)-ornidazole may be one or more diseases selected from the group consisting of complicated and uncomplicated diverticulitis, psuedomembranous colitis, toxigenic *C. difficile* infection, toxigenic *C. difficile* associated diarrhea and accompanying gastroenteritis, cholangitis, cholecystitis, pancreatitis, peritonitis, intra-abdominal/bowel/pelvic/liver abscess, chronic gastritis, gastric cancer, colorectal cancer ulcerative colitis, peptic ulcers, gastroduadenal ulcers, and Crohn's Disease.

In an embodiment, (R)-ornidazole, (S)-ornidazole, and (rac)-ornidazole are for use in treating a condition selected from *H. pylori* infection in biofilm configuration, gastric, dental biofilm (plaque), abdominal and intra-abdominal infections as well as infections with the bacteria in planktonic and intermediate forms.

In an embodiment, the (R)-ornidazole, (S)-ornidazole, and (rac)-ornidazole are for use in treating protozoa infections. In a further embodiment, the protozoa infection is selected from: giardiasis and amoebiasis (e.g. that caused by *Entamoeba histolytica*).

(R)-ornidazole, (S)-ornidazole, and (rac)-ornidazole may also be used in treating trichmoniasis. The trichmoniasis infection may be in men or women.

(R)-ornidazole, (S)-ornidazole, and (rac)-ornidazole may also be used in treating diverticulitis (e.g. complicated diverticulitis). (R)-ornidazole, (S)-ornidazole, and (rac)-ornidazole are highly active against both planktonic and biofilm morphologies of the following bacteria: *Helicobacter pylori*, *Bacteroides* species, *Fusobacterium* species, *Clostridium* species, *Peptococcus* species, *Peptostreptococcus* species, *Eubacterium* species, and *Prevotella* species. These bacterial species are commonly associated with diverticulitis. In particular, (R)-ornidazole, (S)-ornidazole, and (rac)-ornidazole have excellent activity against biofilms of *Bacteroides fragilis*.

In another embodiment the disease is either complicated or uncomplicated diverticulitis which have different treatment paradigms.

(R)-ornidazole, (S)-ornidazole, and (rac)-ornidazole may be used in the treatment of *C. difficile* biofilm infection and may also be used in the treatment of a condition selected from *Clostridium difficile* colitis, infectious diarrhea (e.g. *C. diff.* associated diarrhea (CDAD)), colitis, mucous colitis, and pseudomembranous colitis. These conditions are often caused by *C. difficile* biofilm infections as well as planktonic forms and intermediates. (R)-ornidazole has excellent activity against *C. difficile* and in this invention can be delivered in concentrations high enough to be efficacious for different morphological forms of the bacteria at the site of infection.

In another specific embodiment, the gastrointestinal infection is caused by biofilms of one or more organisms selected from the group consisting of *Prevotella* species, *Bacteroides* species, *Clostridium* species, *Fusobacterium* species, *Helicobacter pylori*, resistant *Helicobacter pylori*, *Peptococcus* species and *Peptostreptococcus* species.

In another specific embodiment, (R)-ornidazole, (S)-ornidazole, and (rac)-ornidazole, or pharmaceutically acceptable salts or esters thereof, are administered in combination with a therapeutically effective amount of one or more other antibiotics for gastrointestinal diseases selected from the group consisting of complicated and uncomplicated diverticulitis, irritable bowel syndrome, pseudomembranous colitis, toxigenic *C. difficile* infection including *C. difficile* which are biofilms, sporulating and in a spore or hard round-body morphological configuration that may be more resistant to concentrations of bacteria determined in vitro assessing the planktonic form of the bacteria, infectious/*Clostridium difficile*-associated diarrhea including those which are toxigenic strains of *C. difficile* which are biofilms, sporulating and in a spore or hard round-body morphological configuration that may be more resistant to concentrations of bacteria determined in vitro assessing the planktonic form of the bacteria, cholangitis, cholecystitis, pancreatitis, peritonitis, intra-abdominal/bowel/pelvic/liver abscess (non-protozoal in origin), ulcerative colitis, chronic gastritis, gastric cancer, colorectal cancer and ulcerative colitis.

Irritable bowel syndrome (IBS) or "spastic colon" is a symptom-based diagnosis characterized by chronic abdominal pain, discomfort, bloating, and alteration of bowel habits. Diarrhea or constipation may predominate, or they may alternate (classified as IBS-D, IBS-C, or IBS-A, respectively). Abnormalities in the gut flora consisting of biofilms and planktonic forms that can be modulated with antibiotics like (R)-ornidazole, (S)-ornidazole, and (rac)-ornidazole result in inflammation and altered bowel function.

Cholangitis, including ascending cholangitis or acute cholangitis is usually caused by bacteria ascending from the junction stomach with the duodenum (first part of the small intestine) forming biofilms. It tends to occur if the bile duct is already partially obstructed by gallstones.

Cholecystitis is inflammation of the gallbladder. Cholecystitis occurs most commonly due to blockage of the cystic duct with gallstones (cholelithiasis).

In another embodiment, the one or more other antibiotics for the gastrointestinal infections are selected from tetracycline antibiotics, macrolide antibiotics, quinolone antibiotics, β-lactam antibiotics and penem antibiotics for co-administration/combination with one of the Ornidazole forms of (R)-ornidazole, (S)-ornidazole, or (rac)-ornidazole.

(R)-ornidazole, (S)-ornidazole, and (rac)-ornidazole may also be used in treating both planktonic and biofilm abdominal and intra-abdominal infections, e.g. severe abdominal and intra-abdominal infections in combination with one or more other antibiotics for gastrointestinal infections. These antibiotics are selected from tetracycline antibiotics, macrolide antibiotics, quinolone antibiotics, β-lactam antibiotics and penem antibiotics.

Abdominal and intra-abdominal infections are mixed infections of gram positive and gram negative aerobic and anaerobic bacteria that typically need antibiotics from several classes to cover all of the potentially pathogenic organism. Specific examples of such abdominal and intra-abdominal infections caused by bacterial biofilms as well as planktonic morphologies include peritonitis, intra-abdominal abscess, and liver abscess. (R)-ornidazole is highly active against both planktonic forms and biofilms of bacterial species including *Bacteroides fragilis*, *Fusobacterium* species, *Clostridium* species, *Peptococcus* species, *Peptostreptococcus* species, *Eubacterium* species, *Prevotella* species. These bacterial species are commonly associated with the above mentioned abdominal and intra-abdominal infections. In particular, (R)-ornidazole, (S)-ornidazole, and (rac)-ornidazole have excellent activity against biofilms of *Bacteroides fragilis* and bacteria that are facultative in their respiration mechanism and morphology.

(R)-ornidazole, (S)-ornidazole, and (rac)-ornidazole may also be used in treating gastroenteritis and chronic gastritis in combination with one or more other antibiotics for gastrointestinal infections where there are mucosal biofilms interacting with epithelial cells. These antibiotics are selected from tetracycline antibiotics, macrolide antibiotics, quinolone antibiotics, β-lactam antibiotics and penem antibiotics.

Gastroenteritis or infectious diarrhea is a medical condition from inflammation of the gastrointestinal tract that involves both the stomach and the small intestine. It causes some combination of diarrhea, vomiting, and abdominal pain and cramping often due to the shedding of planktonic bacteria from biofilms which are sensitive to (R)-ornidazole, (S)-ornidazole, and (rac)-ornidazole.

Chronic gastritis is a histopathologic entity characterized by chronic inflammation of the stomach mucosa caused by bacterial biofilm irritation.

Peptic ulcers and gastroduadenal ulcers are caused by biofilms of *H. pylori* that are sensitive to (R)-ornidazole, (S)-ornidazole, and (rac)-ornidazole which thus can be used to treat or reduce the incidence of these infections in another specific embodiment.

(R)-ornidazole, (S)-ornidazole, and (rac)-ornidazole may also be used in treating Crohn's Disease and ulcerative colitis in combination with one or more other antibiotics for gastrointestinal biofilm infections. These antibiotics are selected from tetracycline antibiotics, macrolide antibiotics, quinolone antibiotics, β-lactam antibiotics and penem antibiotics.

Ulcerative colitis is a form of colitis, a disease of the colon that includes characteristic ulcers, or open sores. The main symptom of active disease is usually constant diarrhea mixed with blood, of gradual onset. The chronic inflammation of the colon mucosa is caused by bacterial biofilm irritation from anaerobes, aerobes, and facultative bacteria.

The methods of the present invention also include treating and/or reducing the incidence of cancer associated with a bacterial biofilm infection; the method comprising administering to a subject in need thereof a therapeutically effective amount of (R)-ornidazole, (S)-ornidazole, and (rac)-ornidazole, or pharmaceutically acceptable salts or esters thereof. The cancers are selected from gastric and colo-rectal cancer and some of the causative pathogens include biofilms of *Helicobacter pylori* for gastric cancer and biofilms of *Fusobacterium* species for colo-rectal cancer.

Another embodiment of the invention includes a method of treatment and/or prophylaxis of cancer associated with a bacterial infection including those infections in a biofilm configuration; the method comprising administering to a subject in need thereof a therapeutically effective amount of (R)-ornidazole, (S)-ornidazole, and (rac)-ornidazole, or pharmaceutically acceptable salts or esters thereof that have activity against organisms associated with cancer such as *Helicobacter pylori* in gastric cancer and *Fusobacterium* species associated with colorectal cancer.

In a specific embodiment, the cancer is colonic cancer or gastric cancer. In another specific embodiment, the the planktonic or bacterial biofilm infection is caused by one or more organisms selected from the group consisting of *Fusobacterium* species, *Helicobacter pylori*, *Peptococcus* species and *Peptostreptococcus* species.

The methods of the present invention also include treating a dermatological condition the method comprising administering to a subject in need thereof a therapeutically effective amount of (R)-ornidazole, (S)-ornidazole, and (rac)-ornidazole, or pharmaceutically acceptable salts or esters thereof.

Another embodiment of the invention includes a method of treating a dermatological condition; the method comprising administering to a subject in need thereof a therapeutically effective amount of (R)-ornidazole, (S)-ornidazole, and (rac)-ornidazole, or pharmaceutically acceptable salts or esters thereof.

In a specific embodiment of the present invention, the dermatological condition is from one or more conditions selected from the group consisting of acne, rosacea, cellulitis, wound infections (e.g. gangrene), boils, cysts, abscesses, fungating tumors, burns, and decubitus ulcers (bed sores).

In an embodiment, the (R)-ornidazole, (S)-ornidazole, and (rac)-ornidazole are for use in treating a dermatological condition. Exemplary dermatological conditions which can be treated using (R)-ornidazole, (S)-ornidazole, and (rac)-ornidazole include one of more of acne, rosacea, fungating tumors, and decubitus ulcers (bed sores).

(R)-ornidazole, (S)-ornidazole, and (rac)-ornidazole may also be used in systemic or topical form for the treatment of rosacea. Rosacea has been associated with an inflammation causing mite that feeds on biofilms of *Bacillus oleronius* in the pores of human skin.

Another embodiment of the invention includes therapeutic uses of (R)-ornidazole, (S)-ornidazole, and (rac)-ornidazole, or pharmaceutically acceptable salts or esters thereof, in different oral, topical, and parenteral formulations for the treatment of a dermatological condition (e.g. one or more of rosacea, fungating tumors, and decubitus ulcers).

(R)-ornidazole, (S)-ornidazole, and (rac)-ornidazole may also be used in the treatment of fungating tumors.

(R)-ornidazole, (S)-ornidazole, and (rac)-ornidazole may also be used in the treatment of decubitus ulcers (bed sores).

In another embodiment, the dermatological condition is caused by one or more organisms selected from the group consisting of biofilms of *Bacillus oleronius*, *Peptococcus* species *Bacteroides* species, *Prevotella* species and *Peptostreptococcus* species.

In another embodiment, (R)-ornidazole, (S)-ornidazole, and (rac)-ornidazole, or pharmaceutically acceptable salts or esters thereof, are administered topically. For example, (R)-ornidazole, (S)-ornidazole, and (rac)-ornidazole, or pharmaceutically acceptable salts or esters thereof, are administered topically for the treatment of rosacea.

(R)-ornidazole, (S)-ornidazole, and (rac)-ornidazole may also be used in treating skin infections (e.g. complicated and uncomplicated skin infections). Specific examples of such skin infections include diabetic foot ulcers and surgical wound infections which are associated with biofilms of gram negative anaerobic pathogens and facultative anaerobic pathogens.

The methods of the present invention also include treating Lyme Disease; the method comprising administering to a subject in need thereof a therapeutically effective amount of (R)-ornidazole, (S)-ornidazole, and (rac)-ornidazole, or pharmaceutically acceptable salts or esters thereof.

Another embodiment of the invention includes therapeutic uses of (R)-ornidazole, (S)-ornidazole, and (rac)-ornidazole, or pharmaceutically acceptable salts or esters thereof, in different oral, topical and parenteral formulations for the treatment of bacterial infections including Lyme disease (e.g. that caused by *Borrelia burgdorferi*). (R)-ornidazole, (S)-ornidazole, and (rac)-ornidazole, or pharmaceutically acceptable salts or esters thereof, may be in combination with one or more antibiotics in the tetracycline, beta lactam (penicillin & cephalosporin) and macrolide classes of antibiotics where there is a likelihood of the presence of the cystic form of the bacteria as well as other forms highly sensitive to these other classes of drugs.

Another embodiment of the present invention includes a method of treating both spirochete forms, hard body/cystic forms, and biofilm forms of Lyme Disease; the method comprising administering to a subject in need thereof a therapeutically effective amount of (R)-ornidazole, (S)-ornidazole, and (rac)-ornidazole, or pharmaceutically acceptable salts or esters thereof.

In another specific embodiment, the Lyme Disease is caused by *Borrelia* spirochetes and at least some of the *Borrelia* spirochetes are present in biofilm or a hard round body or cystic form. In another specific embodiment, the (R)-ornidazole, (S)-ornidazole, and (rac)-ornidazole, or pharmaceutically acceptable salts or esters thereof, are administered in combination with a therapeutically effective amount of one or more antibiotics selected from the group consisting of tetracycline, and or β-lactam antibiotics, and or macrolide antibiotics. In another specific embodiment, the β-lactam antibiotics are selected from one or more of the group consisting of penicillin and cephalosporin. In another specific embodiment, the macrolide antibiotics are selected from one or more of the group consisting of erythromycin, clarithromycin, and azithromycin. The tetracycline antibiotic may be doxycycline.

(R)-ornidazole, (S)-ornidazole, and (rac)-ornidazole may also be used for treating Lyme Disease. (R)-ornidazole, (S)-ornidazole, and (rac)-ornidazole may be for use in treating infections caused by *Borrelia spirochete* bacteria e.g. one or more of *Borrelia burgdorferi* sensu lato (which includes the three genospecies *Borrelia burgdorferi* sensu strict, *Borrelia garinii*, and *Borrelia afzelii*). Such bacteria cause a range of infections including Lyme Disease. (R)-ornidazole, (S)-ornidazole, and (rac)-ornidazole are particularly useful in treating infections (e.g. Lyme Disease) caused by *Borrelia* in biofilms and in a hard body or cystic form, something that many other classes of antibiotic drugs cannot do. The biofilm and cystic form results in a very long latent stage of Lyme Disease and a reduction or elimination of such forms would be expected to be beneficial in the treatment of the disease.

(R)-ornidazole, (S)-ornidazole, and (rac)-ornidazole combination products are particularly effective in treating Lyme Disease which is in a mixed form, e.g. Lyme disease in which the spirochetes are present in either a biofilm or a cystic form and in another form (e.g. a corkscrew form). Thus, compositions of the invention may be used to treat instances of Lyme disease in which at least some of the spirochetes are present in a cystic form or biofilm form.

In a particular embodiment, (R)-ornidazole, (S)-ornidazole, and (rac)-ornidazole are used to treat joint infections associated with Lyme Disease, for example infection of the synovial tissue and joint fluid. As such the treatment of Lyme disease with (R)-ornidazole, (S)-ornidazole, and (rac)-ornidazole may be effecting in treating or alleviating symptoms of some of the clinical manifestations of Lyme disease such as Lyme arthritis, resulting in reduction or elimination of, for example, joint and/or muscle pain or joint swelling associated with the infection.

The methods of the present invention also include treating a disease, the method comprising administering to a subject in need thereof a therapeutically effective amount of (R)-or (R)-ornidazole, (S)-ornidazole, and (rac)-ornidazole nidazole, or pharmaceutically acceptable salts or esters thereof; wherein the disease is selected from one or more diseases selected from the group consisting of Glanders and Melioidosis infections.

In another embodiment, the (R)-ornidazole, (S)-ornidazole, and (rac)-ornidazole, or pharmaceutically acceptable salts or esters thereof, are used to treat the Glanders or Melioidosis infections are caused by biofilms of *Burkholderia mallei* or *Burkholderia pseudomallei* and at least some of the bacteria are present in an aneroebic configuration.

In another embodiment, the (R)-ornidazole, (S)-ornidazole, and (rac)-ornidazole, or pharmaceutically acceptable salts or esters thereof, that are used to treat the Glanders or Melioidosis infections caused by biofilms *Burkholderia mallei* or *Burkholderia pseudomallei* are used in combination with one or more antibiotics, the antibiotics being selected from β-lactam antibiotics, tetracycline antibiotics, penem antibiotics, quinolone antibiotics and macrolide antibiotics. These antibiotics will be active against the bacteria while it is in an aerobic format for its respiration while (R)-ornidazole, (S)-ornidazole, and (rac)-ornidazole will be active against the bacteria while they are in an anaerobic format for their respiration.

The methods of the present invention also include treating a disease, the method comprising administering to a subject in need thereof a therapeutically effective amount of (R)-ornidazole, (S)-ornidazole, and (rac)-ornidazole, or pharmaceutically acceptable salts or esters thereof; wherein the disease is Q-fever.

In another embodiment, the (R)-ornidazole, (S)-ornidazole, and (rac)-ornidazole, or pharmaceutically acceptable salts or esters thereof, are used to treat the Q fever infection caused by *Coxiella burnetii*, a bacterium that affects humans and other animals, and at least some of the bacteria are a spore-like small cell variant, and are obligate intracellular pathogens.

In another embodiment, (R)-ornidazole, (S)-ornidazole, and (rac)-ornidazole, or pharmaceutically acceptable salts or esters thereof, that is used to treat Q-fever is for use in combination with one or more antibiotics, the antibiotics being selected from β-lactam antibiotics, tetracycline antibiotics, penem antibiotics, quinolone antibiotics and macrolide antibiotics that can contribute to the killing of the *Coxiell burnetti* bacteria that take sanctuary in the highly acidic vacuoles of the human host's macrophages in the gastrointestinal track.

The methods of the present invention also include treating a disease, the method comprising administering to a subject in need thereof a therapeutically effective amount of (R)-ornidazole, (S)-ornidazole, and (rac)-ornidazole, or pharmaceutically acceptable salts or esters thereof; wherein the disease is selected from one or more diseases selected from the group consisting of systemic and cardiovascular infections, bone and joint infections, CNS infections, upper and lower respiratory infections and lung infections. In a specific embodiment, the disease is selected from: septicemia, septic shock, bacteremia, endocarditis, indwelling catheter or device infections, osteomyelitis, joint infection, septic arthritis, meningitis, encephalitis, brain abscess, sinusitis, tonsillitis, lung abscess, emphysema, pneumonia, (including nosocomial, aspiration and community acquired pneumonia), bronchitis. In another specific embodiment, the disease is caused by one or more organisms selected from the group consisting of morphological forms, including biofilms, of *Prevotella* species, *Peptococcus* species, *Bacteroides* species, *Clostridium* species and *Peptostreptococcus* species.

Another embodiment of the invention includes a method of treating a disease, the method comprising administering to a subject in need thereof a therapeutically effective amount of (R)-ornidazole, (S)-ornidazole, and (rac)-ornidazole, or pharmaceutically acceptable salts or esters thereof; wherein the disease is selected from: systemic and cardiovascular infections, bone and joint infections, CNS infections, upper and lower respiratory infections and lung infections.

In another specific embodiment, (R)-ornidazole, (S)-ornidazole, and (rac)-ornidazole, or pharmaceutically acceptable salts or esters thereof, is administered in combination with a therapeutically effective amount of one or more other antibiotics for cardiovascular infections, bone and joint infections, CNS infections, upper and lower respiratory infections and lung infections. In another specific embodiment, the one or more other antibiotics are selected from tetracycline antibiotics, macrolide antibiotics, quinolone antibiotics, β-lactam antibiotics and penem antibiotics.

In an embodiment, (R)-ornidazole, (S)-ornidazole, and (rac)-ornidazole may also be used in treating heart infections. A specific example of such cardiac infections is endocarditis.

In an embodiment, (R)-ornidazole, (S)-ornidazole, and (rac)-ornidazole may also be used in treating central nervous system infections. Specific examples of such central nervous system infections include meningitis, brain abscesses, and a bacterial dysbiosis that exacerbate the symptoms of autism and Parkinson's disease.

In an embodiment, (R)-ornidazole, (S)-ornidazole, and (rac)-ornidazole may also be used in treating blood infections. Specific examples of such blood stream infections include bacteremia and septicemia.

In an embodiment, (R)-ornidazole, (S)-ornidazole, and (rac)-ornidazole may also be used in treating bone and joint infections.

In an embodiment, (R)-ornidazole, (S)-ornidazole, and (rac)-ornidazole may also be used in treating lung infections. Specific examples of such pulmonary infections include one or more of emphysema, pneumonia & aspiration pneumonia, Lemmiere's Syndrome, and lung abscess.

Another embodiment of the invention includes a method of preventing the transmission of a sexually transmitted disease; the method comprising administering to a subject in need thereof a therapeutically effective amount of (R)-ornidazole, (S)-ornidazole, and (rac)-ornidazole, or a pharmaceutically acceptable salt or ester thereof.

In an embodiment, (R)-ornidazole, (S)-ornidazole, and (rac)-ornidazole may be used for the reduction of incidence and prevention of sexually transmitted diseases and this transmission related to bacterial vaginosis and/or trichmoniasis and/or vaginal candidiasis. Exemplary sexually transmitted diseases the transmission of which can be prevented according to this invention include human immunodeficiency virus (HIV), herpes simplex virus (HSV), hepatitis C virus (HCV), hepatitis B virus (HBV), human papilloma virus (HPV), gonorrhea, and syphilis, including Yaws, a skin contact transmitted spirochete disease. Bacterial vaginosis, often caused by biofilms of *Gardnerella vaginalis*, and related infections are known to increase the likelihood of STD transmission to women suffering from the infection and from the women to their sexual partners. In particular, (R)-ornidazole, (S)-ornidazole, and (rac)-ornidazole have excellent activity against *Gardnerella vaginalis*. Thus, (R)-ornidazole, (S)-ornidazole, and (rac)-ornidazole may be used to prevent the transmission of sexually transmitted diseases to women and to men.

The methods of the present invention include inhibiting or reducing the incidence of the transmission of a sexually transmitted disease; the method comprising administering to a subject in need thereof a therapeutically effective amount of (R)-ornidazole, (S)-ornidazole, and (rac)-ornidazole, or pharmaceutically acceptable salts or esters thereof.

Another embodiment of the invention includes a method of treating a sexually transmitted disease; the method comprising administering to a subject in need thereof a therapeutically effective amount of (R)-ornidazole, (S)-ornidazole, and (rac)-ornidazole, or pharmaceutically acceptable salts or esters thereof.

In a specific embodiment, the disease that may be treated by (R)-ornidazole, (S)-ornidazole, and (rac)-ornidazole may be one or more diseases selected from the group consisting of biofilms of syphilis, yaws (transmitted by non-sexual contact), and bacterial urethritis in men or women.

In an embodiment, (R)-ornidazole, (S)-ornidazole, and (rac)-ornidazole may also be used in treating bacterial urethritis, particularly in men, but also in women. (R)-ornidazole, (S)-ornidazole, and (rac)-ornidazole are highly active against biofilms of *Gardnerella vaginosis, Bacteroides* species, *Prevotella* species and *Mobiluncus* species that are causative pathogens in bacterial urethritis. In particular, (R)-ornidazole, (S)-ornidazole, and (rac)-ornidazole have excellent activity against biofilms of *Gardnerella vaginalis, Atopobium, Bacteroides* species and *Prevotella* species. The infection of women with bacterial urethritis and the recurrence of bacterial vaginosis is often attributed to transmission of the infection from their male sexual partner with bacterial urethritis. Typically, the woman's male sexual partner would have contracted the infection (in the man it takes the form of bacterial urethritis or similar) from a woman, possibly is regular female sexual partner or possible from a different partner. Bacterial urethritis is often asymptomatic in men. Thus, (R)-ornidazole, (S)-ornidazole, and (rac)-ornidazole may be used in either the treatment or the prophylaxis of bacterial urethritis and the prophylaxis of vaginosis, by administering (R)-ornidazole, (S)-ornidazole, and (rac)-ornidazole in a therapeutically effective dose to a subject's sexual partner. Of course, typically the treatment and the prophylaxis of bacterial vaginosis will be conducted simultaneously by administering to a subject and to a subject's sexual partner a therapeutically effective amount of (R)-ornidazole, (S)-ornidazole, and (rac)-ornidazole. Thus, the (R)-ornidazole, (S)-ornidazole, and (rac)-ornidazole may be used in the treatment or prophylaxis of bacterial urethritis, particularly in men who are the sexual partners of women suffering from bacterial urethritis or bacterial vaginosis. Prophylactic treatment of a male sexual partner of an infected woman may be beneficial in preventing or reducing the risk of transmission of infection to the male partner.

In a specific embodiment, (R)-ornidazole, (S)-ornidazole, and (rac)-ornidazole may used in men in a single 1.5 gram dose for the treatment and prophylaxis of bacterial urethritis and the prophylaxis of bacterial urethritis and bacterial vaginosis in the male's female sexual partner. Since the infection is men is asymptomatic, this single dose regimen will gain far greater compliance/adherence than in multiple dose regimens and will thus be more effective in treating infection and preventing transmission to new partners.

Another embodiment of the invention includes a method of treatment and/or reduction of incidence/prophylaxis of a gynecological, genitourinary or vaginal infection; the method comprising administering to a subject in need thereof a therapeutically effective amount of (R)-ornidazole, (S)-ornidazole, and (rac)-ornidazole, or a pharmaceutically acceptable salt or ester thereof.

In a specific embodiment, the methods include treating and/or reducing the incidence of a gynecological, genitourinary or vaginal infection; the method comprising administering to a subject in need thereof a therapeutically effective amount of (R)-ornidazole, (S)-ornidazole, and (rac)-ornidazole, or pharmaceutically acceptable salts or esters thereof. Such infections include one or more of vulvovaginitis, bacterial vaginosis, vaginal candidiasis (yeast infections) (e.g. mixed infections which include vaginal candiasis), and trichomoniasis.

In another specific embodiment, the gynecological, genitourinary or vaginal infection is selected from one or more infections/diseases selected from the group consisting of bacterial vaginosis, vulvovaginitis, vaginal candidiasis (yeast infections), bacterial urethritis, protozoal urethritis, sexually transmitted urethritis, cystitis, pyleonephritis, prostatitis, urosepsis, urinary tract infections, trichomoniasis, endometritis, endomyometritis, tubo-ovarian abscess, gynecological infection resulting in premature rupture of membrane in pregnancy and pre-term labor (PRM/PTL), pelvic inflammatory disease (PID) and postsurgical vaginal cuff infection.

Thus, the genitourinary infection may be selected from one or more infections/diseases selected from the group consisting of: bacterial vaginosis, bacterial urethritis, prostatitis, urosepsis, urinary tract infections, endometritis, endomyometritis, tubo-ovarian abscess, gynecological infection resulting in premature rupture of membrane in pregnancy/pre-term labor (PRM/PTL), pelvic inflammatory disease (PID) and postsurgical vaginal cuff infection. In a further embodiment the infection is selected from endometritis, endomyometritis, tubo-ovarian abscess, gynecological infection resulting in premature rupture of membrane in pregnancy (PRM/PTL) pelvic inflammatory disease (PID) and postsurgical vaginal cuff infection.

(R)-ornidazole, (S)-ornidazole, and (rac)-ornidazole may also be used in treating bacterial vaginosis. (R)-ornidazole, (S)-ornidazole, and (rac)-ornidazole are highly active against biofilms of *Gardnerella vaginosis, Bacteroides* species, *Prevotella* species, and *Mobiluncus* species.

In a further specific embodiment the infection is PID. In a further embodiment the infection is selected from endometritis, endomyometritis, tubo-ovarian abscess, gynecological infection resulting in premature rupture of membrane in pregnancy (PRM/PTL) preterm labor, and postsurgical vaginal cuff infection.

In another specific embodiment, the gynecological, genitourinary or vaginal infection is caused, at least in part, by one or more organisms selected from the group consisting of biofilms of *Gardnerella vaginalis, Mobiluncus curtisii, Prevotella* species, *Bacteroides* species, *Atopobium vaginae, Peptococcus* species, *Peptostreptococcus* species, *Clostridium* species and *Trichomonas vaginalis*.

In another specific embodiment, the (R)-ornidazole, (S)-ornidazole, and (rac)-ornidazole, or pharmaceutically acceptable salts or esters thereof is administered in combination with a therapeutically effective amount of an antifungal drug.

In another specific embodiment, (R)-ornidazole, (S)-ornidazole, and (rac)-ornidazole, or pharmaceutically acceptable salts or esters thereof are administered in combination with a therapeutically effective amount of an antifungal drug.

In another specific embodiment, the co-administered antifungal drug is topically administered to the vagina.

In another specific embodiment, the co-administered antifungal drug is administered systemically.

In another specific embodiment, the antifungal drug is selected from: azole antifungal drugs, triazole antifungal drugs, thiazole antifungal drugs and echinocandin antifungal drugs, or a combination thereof. In another specific embodiment, the antifungal drug is selected from: fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin and their pharmaceutically acceptable salts, or a combination thereof.

In another specific embodiment of the invention, the methods include administering (R)-ornidazole, (S)-ornidazole, and (rac)-ornidazole, or pharmaceutical salts or esters thereof topically to the vagina. In another specific embodiment, (R)-ornidazole, (S)-ornidazole, and (rac)-ornidazole, or pharmaceutical salts or esters thereof, are administered systemically.

The methods of the present invention also include treating odontogenic, dental and periodontal infections; the method comprising administering to a subject in need thereof a therapeutically effective amount of (R)-ornidazole, (S)-ornidazole, and (rac)-ornidazole, or pharmaceutically acceptable salts or esters thereof.

In a specific embodiment, the infection is selected from: dental carries, peri-apical abscess, periodontal abscess, and acute peri-coronitis of impacted or partially erupted teeth.

In another embodiment, the infection is caused by one or more organisms selected from the group consisting of biofilms of *Prevotella* species, *Peptococcus* species, *Peptostreptococcus* species, *Porphryomonas* species, *Bacteroides* species, *Clostridium* species, *Fusobacterium* species, *Streptococcus* species, *Treponema* species, *Lactobacilli* species and *Actinomyces* species.

In another specific embodiment, the (R)-ornidazole, (S)-ornidazole, and (rac)-ornidazole, or pharmaceutically acceptable salts or esters thereof, are administered in combination with a therapeutically effective amount of one or more other antibiotics. In another specific embodiment, the one or more other antibiotics are selected from tetracycline antibiotics, macrolide antibiotics, quinolone antibiotics, β-lactam antibiotics and penem antibiotics.

In another embodiment, (R)-ornidazole, (S)-ornidazole, and (rac)-ornidazole may also be used in treating a specific dental or periodontal infection, e.g. a disease selected from: dental carries, peri-apical abscess, periodontal abscess, and acute peri-coronitis of impacted or partially erupted teeth. (R)-ornidazole, (S)-ornidazole, and (rac)-ornidazole are highly active against biofilms of bacterial species including *Bacteroides fragilis*, *Fusobacterium* species, *Peptostreptococcus* species, *Prevotella* species, *Pophyromonas* species, and *Actinomyces* species. These bacterial species are commonly associated with the above mentioned dental and periodontal infections. In particular, (R)-ornidazole, (S)-ornidazole, and (rac)-ornidazole have excellent activity against biofilms of *Bacteroides fragilis*.

The methods of the present invention include treating a bacterial infection, the method comprising administering to a subject in need thereof a therapeutically effective amount of (R)-ornidazole, (S)-ornidazole, and (rac)-ornidazole, or pharmaceutically acceptable salts or esters thereof; wherein the bacterial infection is caused by biofilms or planktonic morphologies of one or more organisms selected from the group consisting of *Helicobacter pylori, Bacteroides fragilis, Bacteroides thetaiotaomicron; Parabacteroidea distasonis, Fusobacterium gonidiaformans, Fusobacterium nucleatum, Prevotella amnii, Prevotella bivia, Prevotella disiens, Prevotella melaninogenica, Prevotella timonensis, Porphyromonas asacharlytica, Porphyromonas gingivalis, Porphyromonas uenonis, Megasphaera*-1, *Megasphaera*-2, *Gardnerella vaginalis, Mobiluncus curtisii, Mobiluncus mulieris, Actinomyces israelii, Actinomyces neui* ssp. anitratus, *Actinomyces neui* ssp. *neui, Actinomyces odontolyticus, Actinomyces radingae, Actinomyces turicensis, Clostridium difficile, Clostridium innocuom, Clostridium perfringens, Clostridium ramosum, Finegoldia magna, Anaerococcus prevotii, Anaerococcus tatradius, Peptostreptococcus anaerobius, Peptoniphilus asaccharolyticus, Peptoniphilus harei, Peptoniphilus lacrimalis* and *Atopobium vaginae*.

In an embodiment, (R)-ornidazole, (S)-ornidazole, and (rac)-ornidazole are for use in treating a disease caused by anaerobic bacteria. In an alternative embodiment, (R)-ornidazole, (S)-ornidazole, and (rac)-ornidazole are for use in treating a disease caused by aerobic bacteria. In an embodiment, (R)-ornidazole, (S)-ornidazole, and (rac)-ornidazole are for use in treating a disease caused by Gram negative bacteria, e.g. a resistant strain of Gram negative bacteria. In an alternative embodiment, (R)-ornidazole, (S)-ornidazole, and (rac)-ornidazole are for use in treating a disease caused by Gram positive bacteria.

In an embodiment, (R)-ornidazole, (S)-ornidazole, and (rac)-ornidazole are for use in treating a disease selected from resistant *H. pylori* infection, (including, but not limited to, metronidazole resistant *H. pylori* infection), odontogenic infections, and Lyme Disease.

In an embodiment, (R)-ornidazole, (S)-ornidazole, and (rac)-ornidazole are for use in treating anaerobic bacterial infections. Such anaerobic bacterial infections include: one or more or urinary tract infections, skin and skin structure infections, abdominal and intra-abdominal infections, ulcerative colitis, diverticulitis, and endometritis. The anaerobic bacterial infection may be caused by a Gram negative anaerobe.

Thus, (R)-ornidazole, (S)-ornidazole, and (rac)-ornidazole may be used in treating urinary tract infections (e.g. complicated and uncomplicated urinary tract infections).

Other bacterial biofilm infections include: *C. difficile* infections, abdominal infections, gastrointestinal infections, dental infections, urinary tract infections, complicated & uncomplicated skin Infections, lung infections, CNS Infections, blood Infections, bone and joint infections, and heart infections.

In an embodiment, (R)-ornidazole, (S)-ornidazole, and (rac)-ornidazole are in combination with one or more other actives.

In an embodiment, (R)-ornidazole, (S)-ornidazole, and (rac)-ornidazole are in combination with a macrolide antibiotic. Exemplary macrolide antibiotics include erythromycin, clarithromycin, & azithromycin.

(R)-ornidazole, (S)-ornidazole, and (rac)-ornidazole may be in combination with an anti-inflammatory agent. Thus, in one embodiment a combination of (R)-ornidazole, (S)-ornidazole, and (rac)-ornidazole and a macrolide antibiotic may be used in combination with an anti-inflammatory agent. Additionally or alternatively (R)-ornidazole, (S)-ornidazole, and (rac)-ornidazole may be in combination with a proton pump inhibitor. Thus, a combination of (R)-ornidazole, (S)-ornidazole, and (rac)-ornidazole and a macrolide antibiotic may be used in combination with a proton pump inhibitor (and/or an anti-inflammatory agent). Exemplary anti-inflammatory agents include mesalazine (which may be in a short or long acting form). Exemplary proton pump inhibitors include omeprazole (e.g. s-omeprazole).

The combination of a proton pump inhibitor and/or an anti-inflammatory agent with (R)-ornidazole (and/or another antibiotic, e.g. a macrolide antibiotic) is expected to alleviate the symptoms of the infection at the same time as the (R)-ornidazole treats the cause of the infection. Among other benefits this can result in increased patient compliance.

In an embodiment, (R)-ornidazole, (S)-ornidazole, and (rac)-ornidazole are used in combination with a quinolone antibiotic, particularly an orally administered quinolone antibiotic. Exemplary quinolone antibiotics include ciprofloxacin, levofloxacin, enoxacin, fleroxacin, & ofloxacin.

In an embodiment, (R)-ornidazole, (S)-ornidazole, and (rac)-ornidazole are used in combination with a tetracycline antibiotic, particularly an orally administered tetracycline antibiotic. An exemplary tetracycline antibiotic is doxycline.

In an embodiment, (R)-ornidazole, (S)-ornidazole, and (rac)-ornidazole are used in combination with an antifungal drug. Exemplary antifungal drugs include those which are active against *Candida albicans*, e.g. azole antifungal drugs, triazole antifungal drugs, thiazole antifungal drugs and echinocandin antifungal drugs, or a combination thereof. More specific antifungal drugs include fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin and their pharmaceutically acceptable salts, or a combination thereof. Thus, the combination of antibacterial and antiprotozoal (R)-ornidazole, (S)-ornidazole, and (rac)-ornidazole with an antifungal drug can prevent secondary super-infections, reduce morbidity and medical expense, and speed recovery. As these indications can also lead to increase risk of STD transmission, eliminating the possibility that any of these interrelated indications return is of utility in limiting the spread of a number of STDs.

In an embodiment, (R)-ornidazole, (S)-ornidazole, and (rac)-ornidazole are used in combination with a β-lactam antibiotic. Exemplary β-lactam antibiotics include amoxillin, cefazolin, cefuroxime, ceftriaxone, cefipime, ceftazidime, & cefoxitin. Further exemplary β-lactam antibiotics include penicillin, amoxiclav, & cephalosporins.

In an embodiment, (R)-ornidazole, (S)-ornidazole, and (rac)-ornidazole are used in combination with a penem antibiotic, such as imipenem.

In an embodiment, (R)-ornidazole, (S)-ornidazole, and (rac)-ornidazole are in a fixed dose combination with the above described antibiotics.

In an embodiment, (R)-ornidazole, (S)-ornidazole, and (rac)-ornidazole are in an oral formulation. If the (R)-ornidazole, (S)-ornidazole, and (rac)-ornidazole are in an oral formulation and it is used in combination with one or more other actives, one or more of the other actives may be in a separate formulation, for example a topical formulation (e.g. a vaginal topical formulation). Alternatively, the one or more other actives may be in the same oral formulation as the (R)-ornidazole, (S)-ornidazole, and (rac)-ornidazole. In a further alternative, the one or more of the other actives are in a different oral formulation to the (R)-ornidazole, (S)-ornidazole, and (rac)-ornidazole.

Alternatively, (R)-ornidazole, (S)-ornidazole, and (rac)-ornidazole may be in a topical formulation (e.g. a vaginal topical formulation or a topical skin semisolid formulation like a cream). If the (R)-ornidazole, (S)-ornidazole, and (rac)-ornidazole are in a topical formulation and it is used in combination with one or more other actives, one or more of the other actives may be in an oral formulation. Alternatively, the one or more other actives may be in the same topical formulation as the (R)-ornidazole, (S)-ornidazole, and (rac)-ornidazole. In a further alternative, the one or more of the other actives are in a different topical formulation to the (R)-ornidazole, (S)-ornidazole, and (rac)-ornidazole.

Another embodiment of the invention includes a method for the prophylaxis and treatment of diseases, the method comprising treating a subject in need thereof with a therapeutically active amount of (R)-ornidazole, (S)-ornidazole, and (rac)-ornidazole, or pharmaceutically acceptable salts or esters thereof.

Another embodiment of the invention includes a pharmaceutical formulation comprising (R)-ornidazole, (S)-ornidazole, and (rac)-ornidazole, or pharmaceutically acceptable salts or esters thereof. The formulation may also comprise a pharmaceutically acceptable excipient (e.g. an adjuvant, diluent or carrier).

Another embodiment of the invention includes a kit comprising a pharmaceutical formulation comprising (R)-ornidazole, (S)-ornidazole, and (rac)-ornidazole, or pharmaceutically acceptable salts or esters thereof, (and optionally at least one other active agent). The kit may also comprise and a separate pharmaceutical formulation comprising at least one other active agent.

Another embodiment of the invention includes the use of (R)-ornidazole, (S)-ornidazole, and (rac)-ornidazole, or pharmaceutically acceptable salts or esters thereof, in a fixed dose combination product with a macrolide antibiotic for the prophylaxis and/or treatment of diseases related to biofilms of one or more of *H. pylori* Infection (including metronidazole resistant *H. pylori* infection), odontogenic, dental and periodontal infections and Lyme Disease (e.g. Lyme disease in which the spirochetes are in their biofilm or cystic form). In this embodiment the fixed dose combination is suitably for the prophylaxis and/or treatment of a disease related to odontogenic, dental and periodontal infections and Lyme Disease (e.g. Lyme disease in which the spirochetes are in their biofilm or cystic form).

Another embodiment of the invention includes the use of (R)-ornidazole, (S)-ornidazole, and (rac)-ornidazole, or pharmaceutically acceptable salts or esters thereof, in a fixed dose combination product with a quinolone antibiotic for the prophylaxis and/or treatment of anaerobic bacterial infections (e.g. one or more of complicated and uncomplicated urinary tract infections, complicated and uncomplicated skin and skin structure infections, abdominal and intra-abdominal infections, Crohn's Disease, diverticulitis (for example complicated diverticulitis), pelvic inflammatory disease, and endometritis).

Another embodiment of the invention includes the use of (R)-ornidazole, (S)-ornidazole, and (rac)-ornidazole, or pharmaceutically acceptable salts or esters thereof, fixed dose drug combinations of oral and topical vaginal formulations of (R)-ornidazole, (S)-ornidazole, and (rac)-ornidazole with different oral and vaginal topical formulations of antifungal drugs (including, but not limited to, fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin and their pharmaceutically acceptable salts, or combination thereof), for the prophylaxis and/or treatment of gynecological and vaginal infections including bacterial vaginosis, vulvovaginitis, vaginal candidiasis (yeast infections), and trichomoniasis.

Another embodiment of the invention includes therapeutic uses of (R)-ornidazole, (S)-ornidazole, and (rac)-ornidazole, or pharmaceutically acceptable salts or esters thereof, in different oral, topical and parenteral formulations for the treatment of bacterial infections including Lyme Disease (e.g. that caused by *Borrelia burgdorferi*). (R)-ornidazole, (S)-ornidazole, and (rac)-ornidazole, or pharmaceutically acceptable salts or esters thereof, may be in combination with one or more antibiotics in the tetracycline or beta lactam (penicillin & cephalosporin) and macrolide classes of antibiotics where there is a likelihood of the presence of the cystic form of the bacteria as well as other forms highly sensitive to these other classes of drugs.

Another embodiment of the invention includes therapeutic uses of (R)-ornidazole, (S)-ornidazole, and (rac)-ornidazole, or pharmaceutically acceptable salts or esters thereof, in different oral, topical, and parenteral formulations for the treatment of a dermatological condition (e.g. one or more of acne, rosacea, fungating tumors, and decubitus ulcers).

Another embodiment of the invention includes therapeutic uses of (R)-ornidazole, (S)-ornidazole, and (rac)-ornidazole, or pharmaceutically acceptable salts or esters thereof, in oral, topical and parenteral formulations for the treatment of bacterial biofilm infections including, but not limited to anaerobic bacterial infections (e.g. one or more of *C. difficile* infections, *H. pylori* infections, abdominal infections, GI infections, dental infections, urinary tract infections, skin infections (e.g. complicated & uncomplicated skin infections), lung infections, CNS infections and conditions, blood infections, bone & joint infections, and heart infections.

Another embodiment of the present invention includes therapeutic uses of (R)-ornidazole, (S)-ornidazole, and (rac)-ornidazole, or pharmaceutically acceptable salts or esters thereof, in a combination product (e.g. a fixed dose combination product) with a beta lactam antibiotic (including, but not limited to amoxillin, cefazolin, cefuroxime, ceftriaxone, cefipime, ceftazidine, & cefoxitin) for the prophylaxis and/or treatment of diseases related to *H. pylori* infection, diverticulitis, gastric, dental, and abdominal and intra-abdominal infections.

Another embodiment of the present invention includes a method of treating a disease selected from: *H. pylori* Infection, odontogenic, dental and periodontal infections and Lyme Disease; the method comprising administering to a subject in need thereof a therapeutically effective amount of (R)-ornidazole, (S)-ornidazole, and (rac)-ornidazole, or pharmaceutically acceptable salts or esters thereof, in combination with a therapeutically effective amount of a macrolide antibiotic.

Another embodiment of the present invention includes a method of treating an anaerobic bacterial infection; the method comprising administering to a subject in need thereof a therapeutically effective amount of (R)-ornidazole, (S)-ornidazole, and (rac)-ornidazole, or pharmaceutically acceptable salts or esters thereof, in combination with a therapeutically effective amount of a quinolone antibiotic.

Another embodiment of the present invention includes a method of treating a gynecological or vaginal infection; the method comprising administering to a subject in need thereof a therapeutically effective amount of (R)-ornidazole, (S)-ornidazole, and (rac)-ornidazole, or pharmaceutically acceptable salts or esters thereof, in combination with a therapeutically effective amount of an antifungal drug.

Another embodiment of the present invention includes a method of preventing the transmission of a sexually transmitted disease; the method comprising administering to a subject in need thereof a therapeutically effective amount of (R)-ornidazole, (S)-ornidazole, and (rac)-ornidazole, or pharmaceutically acceptable salts or esters thereof, in combination with a therapeutically effective amount of an antifungal drug.

Another embodiment of the present invention includes a method of treating Lyme Disease caused by *Borrelia* spirochetes and wherein at least some of the *Borrelia* spirochetes are present a biofilm or cystic form; the method comprising administering to a subject in need thereof a therapeutically effective amount of (R)-ornidazole, (S)-ornidazole, and (rac)-ornidazole, or pharmaceutically acceptable salts or salts thereof, in combination with a therapeutically effective amount of one or more antibiotics, the antibiotics being selected from tetracycline, β-lactam antibiotics and macrolide antibiotics.

Another embodiment of the present invention includes a method of treating a bacterial infection, the method comprising administering to a subject in need thereof a therapeutically effective amount of (R)-ornidazole, (S)-ornidazole, and (rac)-ornidazole, or pharmaceutically acceptable salts or esters thereof; wherein the bacterial biofilm or planktonic infection is caused by an organism selected from: *Bacteroides fragilis, Bacteroides thetaiotaomicron; Parabacteroidea distasonis, Fusobacterium gonidiaformans, Fusobacterium nucleatum, Prevotella amnii, Prevotella bivia, Prevotella disiens, Prevotella melaninogenica, Prevotella timonensis, Porphyromonas asacharlytica, Porphyromonas gingivalis, Porphyromonas uenonis, Megasphaera*-1, *Megasphaera*-2, *Gardnerella vaginalis, Mobiluncus curtisii, Mobiluncus mulieris, Actinomyces israelii, Actinomyces neui* ssp. *anitratus, Actinomyces neui* ssp. *neui, Actinomyces odontolyticus, Actinomyces radingae, Actinomyces turicensis, Clostridium difficile, Clostridium innocuom, Clostridium perfringens, Clostridium ramosum, Finegoldia magna, Anaerococcus prevotii, Anaerococcus tatradius, Peptostreptococcus anaerobius, Peptoniphilus asaccharolyticus, Peptoniphilus harei, Peptoniphilus lacrimalis* and *Atopobium vaginae*.

Other embodiments of the present invention include methods of manufacturing (R)-ornidazole and (S)-ornidazole. In a specific embodiment, the methods include manufacturing (R)-ornidazole and (S)-ornidazole having an enantiomeric purity of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), at least about 95% enantiomeric excess (ee), at least about 96% enantiomeric excess (ee), at least about 97% enantiomeric excess (ee), at least about 98% enantiomeric excess (ee), or at least about 99% enantiomeric excess (ee).

In a specific embodiment, the methods of manufacturing (R)-ornidazole and (S)-ordnidazole include reacting 2-methyl-4(5)-nitroimidazole with (S)-propylene oxide. In a specific embodiment, the reaction is performed in the presence of a Lewis acid. In another specific embodiment, the Lewis acid is $ZnCl_2$. In another specific embodiment, the reaction is performed in the presence of a Bronsted acid. In another embodiment, the Bronsted acid is formic acid. It may be that performing the reaction in the presence of a Lewis Acid rather than a Bronsted acid provides increased reproducibility (e.g. of yield, enantiomeric excess, regioisomeric purity etc.). The present invention also includes the compound (R)-ornidazole having an enantiomeric purity of at least about 95% ee, prepared by a process comprising the step of reacting 2-methyl-4(5)-nitroimidazole with (S)-propylene oxide. The present invention also includes the compound (R)-ornidazole having an enantiomeric purity of at least about 96% ee, prepared by a process comprising the step of reacting 2-methyl-4(5)-nitroimidazole with (S)-propylene oxide. The present invention also includes the compound (R)-ornidazole having an enantomeric purity of at least about 97% ee, prepared by a process comprising the step of reacting 2-methyl-4(5)-nitroimidazole with (S)-propylene oxide. The present invention also includes the compounds (R)-ornidazole and (S)-ornidazole having an enantomeric purity of at least about 98% ee, prepared by a process comprising the step of reacting 2-methyl-4(5)-nitroimidazole with (S)-propylene oxide. The present invention also includes the compound (R)-ornidazole having an enantomeric purity of at least about 99% ee, prepared by a process comprising the step of reacting 2-methyl-4(5)-nitroimidazole with (S)-propylene oxide.

Another embodiment of the invention includes a method of manufacturing (R)-ornidazole and (S)-ornidazole; the method comprising reacting 2-methyl-4(5)-nitroimidazole with (S)-propylene oxide.

In an embodiment, the reaction is performed in the presence of a Lewis acid. In a further embodiment, the Lewis acid is $ZnCl_2$.

In an alternative embodiment, the reaction is performed in the presence of a Bronsted acid. In a further embodiment, the reaction is performed in the presence of formic acid. In some embodiments, the acid may also be the reaction solvent.

In an embodiment, the reaction is conducted in an ether solvent (e.g. diethyl ether, THF, $^t$BuOMe). In a further embodiment, the reaction is conducted in THF. This embodiment applies particularly to embodiments in which the reaction is conducted in the presence of a Lewis acid.

In an embodiment, the reaction was conducted at a reduced temperature. In a further embodiment, the reaction was conducted at a temperature of about 10° C. In an embodiment, the reaction was conducted at a temperature from about 0 to about 25° C. Thus, the reaction was conducted at a temperature from about 5 to about 15° C. Specifically, the reaction was conducted at a temperature from about 7 to about 13° C.

This is a more efficient process than the one previous enantioselective synthesis of Ornidazole enantiomers (CN 101108828) which requires pre-activation of 2-methyl-4(5)-nitroimidazole before reaction with the chiral side chain precursor. On the other hand, the present invention provides a one-step, one-pot enantioselective synthesis of (R)-ornidazole or (S)-ornidazole. In some embodiments, due to the methods of manufacturing, the (R)-ornidazole and (S)-ornidazole, or a pharmaceutically acceptable salts or esters thereof, have an enantiomeric purity of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), at least about 95% enantiomeric excess (ee), at least about 96% enantiomeric excess (ee), at least about 97% enantiomeric excess (ee), at least about 98% enantiomeric excess (ee), or at least about 99% enantiomeric excess (ee).

Any of the embodiments described above for the first aspect of the invention may equally apply to any of the subsequent aspects of the invention. In addition, any embodiment may also apply to any other embodiments. In other words, the features described in the above embodiments of the invention can be combined.

BRIEF DESCRIPTION OF THE DRAWINGS

Embodiments of the invention are further described hereinafter with reference to the accompanying drawings, FIG. 1, in which stereo-selective syntheses are described.

DETAILED DESCRIPTION OF THE INVENTION

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

In any aspect or embodiment of the invention described in this specification, the (R)-ornidazole may be in the form of a pharmaceutically acceptable salt (e.g. the HCl salt) or ester. Alternatively, the (R)-ornidazole may be present as a free base, i.e. not in the form of a salt. The (R)-ornidazole, or pharmaceutically active salt or ester thereof, may be in the form of a hydrate.

Likewise, many of the embodiments of the invention are concerned with combinations of (R)-ornidazole, (S)-ornidazole, and (rac)-ornidazole with one or more other active agents. Where appropriate, and irrespective of whether (R)-ornidazole, (S)-ornidazole, and (rac)-ornidazole are in the form of a pharmaceutically acceptable salts, any one or more of the other active agents may be in the form of a pharmaceutically acceptable salt.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

It is intended that the aspects and embodiments of this invention encompasses (R)-ornidazole and/or any other active agent in all solid forms, including amorphous forms, as well as crystalline forms, and polymorphs thereof.

By (S) enantiomer is intended to mean that enantiomer which produces a positive optical rotation. This has been shown, through independent synthesis, to be the (S)-enantiomer and is identified as such throughout this specification. In the unlikely event that this assignment has been done in error, this specification is directed to (+)-Ornidazole.

This invention relates to various uses and syntheses of (R)-ornidazole. In this context (R)-ornidazole is not intended to refer only to pure (S)(+)-Ornidazole but also to Ornidazole in which the (S)(+)-enantiomer predominates over the (R)(−)-enantiomer. Thus, the term (S)(+)-senidazole also includes mixtures in which there is a small amount (e.g. less than 10% by weight, e.g. less than 5% by weight) of (R)(−)-Ornidazole.

The term "(S)(+)-senidazole" thus includes (S)(+)-Ornidazole by itself or when it is available in an enantiomeric excess over the (R)(−)-Ornidazole enantiomer.

Macrolide antibiotics are antibiotics which comprise a large (e.g. 14-, 15- or 16-membered) macrocyclic lactone ring. Exemplary macrolide antibiotics include: dirithromycin, roxithromycin, telithromycin, erythromycin, clarithromycin, & azithromycin and in particular erythromycin, clarithromycin, & azithromycin.

β-Lactam antibiotics are antibiotics in which the structure features a β-lactam moiety. They include cefalosporins (e.g.corecefazolin, cefacetrile, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefbuperazone, cefuroxime, cefuzonam, cefoxitin, cefotetan, cefmetazole, flomoxef, loracarbef, cefixime, ceftazidime, ceftriaxone, cefcapene, cefdaloxime, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, latamoxef, cefepime, cefozopran, cefpirome, cefquinome, ceftobiprole, ceftaroline, cefdinir, cefprozil, cefalexin), penems (e.g. faropenem, biapenem, doripenem, ertapenem, imipenem, meropenem, panipenem) and penicillin derivatives (e.g. amoxillin and penicillin). Exemplary β-lactam antibiotics include amoxillin, amoxiclav, cefazolin, cefuroxime, ceftriaxone, cefipime, ceftazidine, & cefoxitin. Further exemplary β-lactam antibiotics include penicillin & cephalosporin.

Quinolone antibiotics (which include the fluoroquinolone antibiotics) are antibiotics with a quinolone (or aza-quinolone) backbone. They include enoxacin, fleroxacin, lomefloxacin, nadifloxacin, norfloxacin, rufloxacin, balofloxacin, grepafloxacin, pazufloxacin, sparfloxacin, temafloxacin, tosufloxacin, besifloxacin, clinafloxacin, garenoxacin, gemifloxacin, gatifloxacin, sitafloxacin, trovafloxacin, prulifloxacin, ciprofloxacin, levofloxacin and ofloxacin. Exemplary quinolone antibiotics include ciprofloxacin, levofloxacin, enoxacin, fleroxacin, & ofloxacin.

Where antibiotics (and particularly quinolone antibiotics) are used in combination with (R)-ornidazole, the antibiotic will typically be administered orally.

Proton pump inhibitors slow the production of gastric acid. Examples include omeprazole, lansoprazole, dexlansoprazole, esomeprazole, pantoprazole, rabeprazole, ilaprazole. A particular proton pump inhibitor suitable for use in the combinations of the invention is omeprazole (e.g. s-omeprazole).

Antiinflammatory agents may be steroidal (e.g. corticoids) or non-steroidal (e.g. aspirin, ibuprofen, mesalazine). An particular anti-inflammatory agent suitable for use in the combinations of the invention is mesalazine. Antifungal agents suitable for use in the combinations of the invention include: fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin.

Throughout this specification, the terms aerobic and anaerobic bacteria are used to describe the bacterial species against which (R)-ornidazole, (S)-ornidazole, and (rac)-ornidazole are active against. Bacterial species may be obligate aerobic species or they may be non-obligate aerobic species. Likewise, bacterial species can be obligate anaerobic species or non-obligate species. Sometimes, an obligate aerobic species is able to survive in anaerobic conditions by the actions of accompanying anaerobic bacteria. (R)-ornidazole is useful against biofilm infections caused by any or all of the above bacteria.

Throughout this specification the term 'in combination' means that either (R)-ornidazole, (S)-ornidazole, or (rac)-ornidazole and the one or more other actives are both administered to the patient over the same period of treatment. They may be administered together, i.e. at the same time. In this case they may be administered in a single formulation, (e.g. as a single tablet or capsule or sachet) or in separate formulations administered simultaneously or nearly simultaneously. Alternatively, they may be administered at separate times of day. Where the (R)-ornidazole, (S)-ornidazole, and (rac)-ornidazole and other active(s) are administered separately it is to be under stood that the timing of separate dosing is selected such that the beneficial effect of the first administered agent is not lost prior to administration of the second or further agent. Whatever the precise timing of the administration, (R)-ornidazole, (S)-ornidazole, and (rac)-ornidazole and the one or more other actives may be administered via different means, e.g. the (R)-ornidazole may be administered in an oral formulation and the other active may be administered as a topical formulation or vice versa.

The combinations of the invention provide benefits which are at least additive compared to the use of either agent alone. In many embodiments, the combinations are something more than additive e.g. synergistic compared to the use of either agent alone.

References to kits in this specification where (R)-ornidazole, (S)-ornidazole, and (rac)-ornidazole, or pharmaceutically acceptable salts or esters thereof, is used in kit form with one or more different active agents optionally further comprise instructions for the administration of the (R)-ornidazole, (S)-ornidazole, and (rac)-ornidazole, or pharmaceutically acceptable salts or esters thereof, and the other active agent(s) in the kit.

The definition of the term 'treatment' in this specification encompasses prophylaxis and prevention (i.e. reducing or eliminating the risk of contracting the disease). As well as meaning curing a person of the disease, 'treatment' also includes preventing the onset of symptoms, controlling (e.g. by slowing or eliminating) progression of disease, preventing the spread of the disease to other parts of the body and/or to other persons, reducing the spread of the disease and other facets of medical practice which will be readily understood by the person skilled in the art to fall within the meaning of the term 'treatment'.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Formulations

For the above-mentioned therapeutic uses the dosage administered will, of course, vary with the compound employed, the mode of administration, the treatment desired and the disorder indicated. For example, if the (R)-ornidazole is administered orally, then the daily dosage of the compound of the invention may be in the range from 0.01 micrograms per kilogram body weight (μg/kg) to 100 milligrams per kilogram body weight (mg/kg). In a specific embodiment, the formulations for administration to a subject contain about 2.0 g of (R)-ornidazole, about 1.5 g of (R)-ornidazole, about 1 g of (R)-ornidazole, about 0.5 g of (R)-ornidazole, about 0.4 g of (R)-ornidazole. 0.3 g of (R)-ornidazole, 0.2 g of (R)-ornidazole, and about 0.1 g of (R)-ornidazole. This is also true of the (S) enantiomer of Ornidazole [(S)-ornidazole] and the Ornidazole racemic mixture.

The beneficial properties of (R)-ornidazole, (S)-ornidazole, and (rac)-ornidazole include a favorable pharmacokinetic and pharmacodynamic profile. (R)-ornidazole and (S)-ornidazole are components of rac-ornidazole and have similar, but slightly improved PK profiles. Indeed, In particular embodiments, after administration of rac-Ornidazole in a formulation, the $T_{max}$ of rac-Ornidazole ranges about 2 hours to about 4 hours inclusive of all ranges therebetween.

In another embodiment, after administration of rac-ornidazole in a formulation, the $C_{max}$ of rac-ornidazole ranges (after single administration) from about 9 mg/L to about 31.5 mg/L, inclusive of all ranges therebetween.

In another specific embodiment, rac-ornidazole concentrations, including the (R)-ornidazole and (S)-ornidazole components, have been measured in the colonic (8.7 mg/g) and abdominal (3.6 to 4.4 mg/g) walls and epiploic fat (3.4 to 4.7 mg/g) throughout colorectal surgery in those receiving a 1 g intravenous dose for surgical prophylaxis. In another study, concentrations were measured in epiploic fat (2.48 to 4.64 mg/g) throughout liver transplantation after a 500 mg intravenous dose was given together with ceftriaxone 1 g for surgical prophylaxis. Penetration rates for this study compared with plasma concentrations ranged between 50 and 70%.

In another embodiment, after a single administration of rac-ornidazole in a formulation, the present invention provides an $AUC_{0-\infty}$ for rac-ornidazole of about 185 to about 375 mg-hr/L, and about 500 to about 511 mg-hr/L, inclusive of all ranges there between. The AUC for the (R)-ornidazole and (S)-ornidazole components are similar.

In another embodiment, after a single administration of rac-ornidazole in a formulation, the elimination half-life ($T_{1/2}$) of rac-ornidazole is about 14 hours to about 18 hours. The ($T_{1/2}$) of the (R)-ornidazole and (S)-ornidazole components are similar.

(R)-ornidazole, (S)-ornidazole, and (rac)-ornidazole, or pharmaceutically acceptable salts or esters thereof, may be used on their own but will generally be administered in the form of a pharmaceutical composition in which the (R)-ornidazole, (S)-ornidazole, and (rac)-ornidazole, or pharmaceutically acceptable salts thereof, are in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of (R)-ornidazole, (S)-ornidazole, and (rac)-ornidazole, the pharmaceutical composition which is used to administer (R)-ornidazole, (S)-ornidazole, and (rac)-ornidazole will preferably comprise from 0.05 to 99% w (percent by weight) (R)-ornidazole, (S)-ornidazole, and (rac)-ornidazole, more preferably from 0.05 to 80% w (R)-ornidazole, (S)-ornidazole, and (rac)-ornidazole, still more preferably from 0.10 to 70% w (R)-ornidazole, (S)-ornidazole, and (rac)-ornidazole, and even more preferably from 0.10 to 50% w (R)-ornidazole, (S)-ornidazole, and (rac)-ornidazole, of active ingredient, all percentages by weight being based on total composition.

In many of the embodiments of the invention, (R)-ornidazole, (S)-ornidazole, and (rac)-ornidazole are used in combination with other active agents (e.g. antibiotics, antifungal, anti-inflammatory agent, proton pump inhibitors etc.). Depending on the mode of administration of the other active agent, the pharmaceutical composition used to administer the other active agent (which may or may not be the same pharmaceutical composition which is used to administer (R)-ornidazole, (S)-ornidazole, and (rac)-ornidazole will preferably comprise from 0.05 to 99% w (percent by weight) of the other active agent, more preferably from 0.05 to 80% w of the other active agent, still more preferably from 0.10 to 70% w of the other active agent, and even more preferably from 0.10 to 50% w of the other active agent, of active ingredient, all percentages by weight being based on total composition.

The pharmaceutical compositions may be administered topically (e.g. to the vagina) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

For oral administration (R)-ornidazole, (S)-ornidazole, and (rac)-ornidazole and/or one or more other active agents may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, (R)-ornidazole, (S)-ornidazole, and (rac)-ornidazole and/or one or more other active agents may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration (R)-ornidazole, (S)-ornidazole, and (rac)-ornidazole and/or one or more other active agents may be administered as a sterile aqueous or oily solution. Parenteral formulations are particularly suitable for patients suffering from a severe infections. The person skilled in the art would be well aware of what differentiates a serious infection from a non-serious infection. By way of example, severe infections include those which render the patient unable to take (R)-ornidazole, (S)-ornidazole, and (rac)-ornidazole orally, e.g. infections which render the patient unconscious, emetic, weak, delirious etc. The HCl salt of (R)-ornidazole, (S)-ornidazole, and (rac)-ornidazole are particularly suitable for parenteral administration, e.g. for the treatment of severe infections.

The size of the dose for therapeutic or prophylactic purposes of (R)-ornidazole, (S)-ornidazole, and (rac)-ornidazole and/or one or more other active agents will naturally vary according to the nature and severity of the conditions, the age and sex of the animal or patient and the route of administration, according to well known principles of medicine.

Dosage levels, dose frequency, and treatment durations of (R)-ornidazole, (S)-ornidazole, and (rac)-ornidazole are expected to differ depending on the formulation and clinical indication, age, and co-morbid medical conditions of the patient. In adult patients, as a single agent monotherapy, the daily dose of orally, parentally or rectally administered forms of (R)-ornidazole, (S)-ornidazole, and (rac)-ornidazole are expected to vary from 0.25 g/day-8.0 g/day. Downward dose adjustments from these levels are likely to be needed in infants (0-2 years of age), children (2-18 years of age), and elderly patients (greater than 65 years of age), as well as individuals with renal or liver disease, and upward dose adjustments may be necessary in obese individuals. In adult patients, as a single agent monotherapy, the concentration of topically or vaginally administered forms of (R)-ornidazole, (S)-ornidazole, and (rac)-ornidazole are expected to vary from 0.10-4.0 g/day with the concentration of (R)-ornidazole, (S)-ornidazole, and (rac)-ornidazole in the emollient varying between 0.25%-5%. As a single agent monotherapy, the standard duration of (R)-ornidazole, (S)-ornidazole, and (rac)-ornidazole treatment is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

When (R)-ornidazole, (S)-ornidazole, and (rac)-ornidazole is combined with other medications in fixed dose combinations treatments, the daily dose of orally, parentally, topically, vaginally, or rectally administered forms of (R)-ornidazole, (S)-ornidazole, and (rac)-ornidazole are expected to vary from 0.001 g/day-4.0 g/day.

A specific example of (R)-ornidazole, (S)-ornidazole, and (rac)-ornidazole oral sachet formulations contains (R)-ornidazole, (S)-ornidazole, and (rac)-ornidazole and the following excipients: sugar spheres, Povidone, Polyethylene glycol 4000, Aerosil 200, Talc and Eudragit NE30D. The formulation weighs 4.2 g and contains 2 g of (R)-ornidazole, i.e. the formulation contains about 48% (R)-ornidazole by weight.

Treatment of Gastrointestinal Diseases

In an embodiment, (R)-ornidazole, (S)-ornidazole, and (rac)-ornidazole may also be used in treating gastrointestinal infections.

In an embodiment, the (R)-ornidazole, (S)-ornidazole, and (rac)-ornidazole are for use in treating a condition selected from gastric, dental, abdominal and intra-abdominal infections.

In an embodiment, the (R)-ornidazole, (S)-ornidazole, and (rac)-ornidazole are for use in treating a condition selected from gastric, dental, abdominal and intra-abdominal infections Treatment of C. difficile Infections In one group of embodiments, are provided formulations (e.g. oral or parenteral formulations) comprising (R)-ornidazole, (S)-ornidazole, and (rac)-ornidazole, alone or in combination with other antibiotics including, but not limited to, those in the tetracycline, quinolone, beta lactam, and macrolide classes, for use in treating biofilms of toxigenic C. difficile infections.

C. difficile causes as many as 3 million cases of diarrhea and colitis per year. Some result in life threatening cases of pseudomembranous colitis. (R)-ornidazole, (S)-ornidazole, and (rac)-ornidazole are active against toxigenic Clostridium difficile bacterial infections which cause clinically relevant cases of Clostridium difficile colitis, infectious diarrhea, colitis, mucous colitis, and pseudomembranous colitis. (R)-ornidazole, (S)-ornidazole, and (rac)-ornidazole can therefore be used as an antibiotic to treat these infections and their diarrhea symptoms either alone or in combination with other antibiotics that are active against Clostridium difficile bacteria.

In addition, the pharmacologic parameters of (R)-ornidazole, (S)-ornidazole, and (rac)-ornidazole make them appropriate to use in the setting of the treatment of Clostridium difficile bacterial infections and their related indications. (R)-ornidazole, (S)-ornidazole, and (rac)-ornidazole is rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of oral formulations for these Clostridium difficile bacterial infections including sachet formulations of powder and or pelletized granules, capsules containing the (R)-ornidazole, (S)-ornidazole, and (rac)-ornidazole, oral solid tablet formulations, parenteral, and liquid oral suspension formulations. These include sustained release capsule and tablet and sachet formulations with vehicles for varying absorbencies for delivery to different locations in the gastro-intestinal (GI) tract, capsules containing powders or pelletized granules with these properties, and oral solid tablet formulations with different types of slow release properties. These formulations are particularly appropriate for treatment of gram negative anaerobic bacteria like Clostridium difficile that are resident in the GI tract which is the typical site of infection. In some case, parenteral formulations, such as (R)-ornidazole, (S)-ornidazole, and (rac)-ornidazole in hydrochloride form, are most appropriate for patients in certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings. Additionally topical formulations for skin, dental, and vaginal/urinary tract infections may be appropriate for treatment of infections with these bacteria in those settings and are included in the present invention.

Treatment of Ulcerative Colitis

In one group of embodiments, is provided the use of (R)-ornidazole, (S)-ornidazole, and (rac)-ornidazole in a combination product (e.g. a fixed dose combination product) with a beta lactam antibiotic for the prophylaxis and treatment of ulcerative colitis.

((R)-ornidazole, (S)-ornidazole, and (rac)-ornidazole are highly active against biofilms of Helicobacter pylori, Bacteroides species, Fusobacterium species, Clostridium species, Peptococcus species, Peptostreptococcus species, Eubacterium species, and Prevotella species, some of the bacteria which can contribute to causing clinically relevant cases of ulcerative colitis, and beta lactam antibiotics are active against other causative species of bacteria in ulcerative colitis. Thus, combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

Treatment of Crohn's Disease

In one group of embodiments, is provided the use of (R)-ornidazole, (S)-ornidazole, and (rac)-ornidazole in a combination product (e.g. a fixed dose combination product) with a beta lactam antibiotic for the prophylaxis and treatment of Crohn's Disease.

(R)-ornidazole, (S)-ornidazole, and (rac)-ornidazole are highly active against biofilms of *Helicobacter pylori*, *Bacteroides* species, *Fusobacterium* species, *Clostridium* species, *Peptococcus* species, *Peptostreptococcus* species, *Eubacterium* species, and *Prevotella* species, some of the bacteria which can contribute to causing clinically relevant cases of Crohn's Disease, and beta lactam antibiotics are active against other causative species of bacteria in Crohn's Disease Thus, combination product of (R)-ornidazole, (S)-ornidazole, and (rac)-ornidazole and such other antibiotic(s) are expected to have superior efficacy in the treatment of these indications compared to the use of these agents alone. The combination product can be used as a fixed dose therapeutic in oral sachet, oral solid, and parental formulations.

In addition, the pharmacologic parameters of (R)-ornidazole, (S)-ornidazole, and (rac)-ornidazole make it appropriate to use them in the setting of the treatment the above enumerated bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet, and oral solid tablet formulations with different types of slow release properties.

Treatment of Giardiasis and Amoebiasis

In one group of embodiments, is provided the use of (R)-ornidazole, (S)-ornidazole, and (rac)-ornidazole (e.g. as an oral or parenteral formulation) for the treatment of protozoa infections including, but not limited to, giardiasis and amoebiasis (e.g. that caused by *Entamoeba histolytica* and other species).

*Giardia lamblia* is a flagellated protozoan parasite that colonizes and reproduces in the small intestine, causing giardiasis. The *Giardia* parasite attaches to the epithelium by a ventral adhesive disc, and reproduces via binary fission. Giardiasis does not spread via the bloodstream, nor does it spread to other parts of the gastro-intestinal tract, but remains confined to the lumen of the small intestine. *Giardia* trophozoites absorb their nutrients from the lumen of the small intestine, and are anaerobes. The present invention includes a variety of oral and parenteral formulations of the (R) enantiomer of Ornidazole for the treatment of giardia, including, but not limited to, pelletized powder sachets, capsules, tablets, and IV prefilled syringes.

Amoebiasis refers to infection caused by the amoeba *Entamoeba histolytica*. A gastrointestinal infection that may or may not be symptomatic and can remain latent in an infected person for several years, amoebiasis is estimated to cause 70,000 deaths per year worldwide. Symptoms can range from mild diarrhea to dysentery with blood and mucus in the stool. *E. histolytica* is usually a commensal organism. The present invention, (R)-ornidazole, (S)-ornidazole, and (rac)-ornidazole includes a variety of oral and parenteral formulations of (R)-ornidazole, (S)-ornidazole, and (rac)-ornidazole for the treatment of amoebiasis, including, but not limited to, pelletized powder sachets, capsules, tablets, and IV prefilled syringes.

In addition, the pharmacologic parameters of the (R)-ornidazole, (S)-ornidazole, and (rac)-ornidazole make them appropriate to use in the setting of the treatment of protozoal infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of oral formulations including systemic sachet formulations of powder and or pelletized granules, capsules containing (R)-ornidazole, (S)-ornidazole, and (rac)-ornidazole, oral solid tablet formulations, and liquid oral suspension formulations. These include sachet formulations with vehicles for varying absorbencies for delivery to different locations in the gastro-intestinal (GI) tract, capsules containing powders or pelletized granules with these properties, and oral solid tablet formulations with different types of slow release properties. These formulations are particularly appropriate for treatment of protozoal species.

The beneficial properties of (R)-ornidazole and (S)-ornidazole also include pharmacokinetic and pharmacodynamic benefits related to product dosing verses the racemic mixture of Ornidazole. These benefits will allow formulations utilizing less drug than the racemic mixture so that patients can ingest smaller tablets, capsules, and sachets in some cases, or be able to utilize more convenient dosing schedules of forms, including parenteral formulations, that contain the same amount of drug.

Treatment of Diseases Related to Chronic Gastritis

In one group of embodiments, the present invention provides therapeutic uses of (R)-ornidazole, (S)-ornidazole, and (rac)-ornidazole in a combination product (e.g. a fixed dose combination product) with a macrolide (including, but not limited to erythromycin, clarithromycin, & azithromycin) antibiotic for the prophylaxis and treatment of diseases related to *H. pylori* biofilm infection, (including metronidazole resistant *H. pylori* infection), including, but not limited to chronic gastritis and gastric cancer. Additional embodiments of this fixed dose combination product would also include a proton pump inhibitor (e.g. omeprazole) and or an antiinflammatory agent (e.g. Mesalamine, in a short & long acting version).

In another group of embodiments, are provided formulations (e.g. oral or parenteral formulations) comprising (R)-ornidazole, (S)-ornidazole, and (rac)-ornidazole, alone or in combination with other antibiotics in the quinolone, beta lactam, and macrolide classes, for use in treating *Helicobacter pylori* infections and the diseases that they cause including peptic ulcers & gastroduadenal ulcers, chronic gastritis, gastric cancer and ulcerative colitis.

In yet another group of embodiments, is provided the use of (R)-ornidazole, (S)-ornidazole, and (rac)-ornidazole in a combination product (e.g. a fixed dose combination product) with a beta lactam antibiotic for the prophylaxis and/or treatment of diseases related to *H. pylori* Infection, (including metronidazole resistant *H. pylori* infection).

(R)-ornidazole is highly active against strains of *H. pylori* (including metronidazole resistant strain of *H. pylori*) which cause clinically relevant cases of chronic gastritis and ulcerative colitis and other antibiotics are active against other causative species of bacteria in these infections. Thus, a combination product of (R)-ornidazole, (S)-ornidazole, and (rac)-ornidazole and such other antibiotic(s) is expected to have superior efficacy in the treatment of these indications compared to known actives or the use of these agents alone. The product or combination product can be used as a therapeutic (e.g. fixed dose therapeutic) fixed dose in oral sachet, oral solid, and parental formulations.

In addition, the pharmacologic parameters of (R)-ornidazole, (S)-ornidazole, and (rac)-ornidazole make them appropriate to use in the setting of the treatment of *H. pylori* bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of oral formulations for these *H. pylori* bacterial infections including sachet formulations of powder and or pelletized granules, capsules containing (R)-ornidazole, (S)-ornidazole, and (rac)-ornidazole, oral solid tablet formulations, and liquid oral suspension formulations. These include sachet formulations with vehicles for varying absorbencies for delivery to different locations in the gastro-intestinal (GI) tract, capsules containing powders or pelletized granules with these properties, and oral solid tablet formulations with different types of slow release properties. These formulations are particularly appropriate for treatment of gram negative anaerobic bacteria like *H. pylori* that are resident in the GI tract, the typical site of infections in the above mentioned indications. In some case, parenteral formulations, such as (R)-ornidazole, (S)-ornidazole, and (rac)-ornidazole in hydrochloride form, are most appropriate for patients in certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of Diverticulitis

In one group of embodiments, the present invention provides the use of ((R)-ornidazole, (S)-ornidazole, and (rac)-ornidazole in a combination product (e.g. a fixed dose combination product) with a quinolone (including, but not limited to ciprofloxacin, levofloxacin, enoxacin, fleroxacin, & ofloxacin, for example selected from ciprofloxacin, levofloxacin, enoxacin, fleroxacin, & ofloxacin) antibiotic for the prophylaxis and treatment of simple and complicated diverticulitis.

In another group of embodiments, are provided formulations (e.g. oral or parenteral formulations) comprising (R)-ornidazole, alone or in combination with other antibiotics in the quinolone, beta lactam, and macrolide classes, for use in treating simple and complicated diverticulitis.

In yet another group of embodiments, is provided the use of (R)-ornidazole, (S)-ornidazole, and (rac)-ornidazole in a combination product (e.g. a fixed dose combination product) with a beta lactam antibiotic for the prophylaxis and treatment of simple and complicated diverticulitis.

(R)-ornidazole, (S)-ornidazole, and (rac)-ornidazole are highly active against biofilms of *Helicobacter pylori, Bacteroides* species, *Fusobacterium* species, *Clostridium* species, *Peptococcus* species, *Peptostreptococcus* species, *Eubacterium* species, and *Prevotella* species, some of the bacteria which can contribute to causing clinically relevant cases of diverticulitis, and other antibiotics are active against other causative species of bacteria in diverticulitis. Thus, combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

In addition, the pharmacologic parameters of (R)-ornidazole, (S)-ornidazole, and (rac)-ornidazole make them appropriate to use in the setting of the treatment the above enumerated bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet, and oral solid tablet formulations with different types of slow release properties. In many of severe cases, parenteral formulations, such as (R)-ornidazole, (S)-ornidazole, and (rac)-ornidazole in hydrochloride form, are most appropriate for patients in certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

In the above embodiments relating to the treatment of diverticulitis, the diverticulitis may be uncomplicated diverticulitis or complicated diverticulitis. In particular the diverticulitis is complicated diverticulitis. As described hereinbefore, patients with complicated diverticulitis generally require hospitalisation and infection is confirmed in the diverticuli by for example obtaining a tissue sample from the patients. Generally the patient will require surgery in addition to being treated with (R)-ornidazole, (S)-ornidazole, and (rac)-ornidazole. Patients with diverticulitis may be infected with for example one or more pathogens selected from biofilms of *Prevotella* Species, *Bacteroides* Species, *Fusobacterium* Species, *Helicobacter pylori, Peprococcus* Species and *Peptostreptococcus* Species. Accordingly in a further embodiment of the invention there is provided (R)-ornidazole for use in the treatment of diverticulitis, particularly complicated diverticulitis, in a patient infected by one of more pathogens selected from biofilms of *Prevotella* Species, *Bacteroides* Species, *Fusobacterium* Species, *Helicobacter pylori, Peprococcus* Species and *Peptostreptococcus* Species.

Treatment of Diseases Related to *H. pylori* Infection

In one group of embodiments, the present invention provides therapeutic uses of (R)-ornidazole, (S)-ornidazole, and (rac)-ornidazole in a combination product (e.g. a fixed dose combination product) with a macrolide (including, but not limited to erythromycin, clarithromycin, & azithromycin) antibiotic for the prophylaxis and treatment of diseases related to *H. pylori* Infection, (including metronidazole resistant *H. pylori* infection), including, but not limited to peptic ulcers & gastroduadenal ulcers, chronic gastritis gastic cancer, and Crohn's Disease. Additional embodiments of this fixed dose combination product would also include a proton pump inhibitor (e.g. omeprazole) and or an antiinflammatory agent (e.g. Mesalamine, in a short & long acting version).

In another group of embodiments, are provided formulations (e.g. oral or parenteral formulations) comprising (R)-ornidazole, (S)-ornidazole, and (rac)-ornidazole, alone or in combination with other antibiotics in the quinolone, beta lactam, and macrolide classes, for use in treating *Helicobacter pylori* infections and the diseases that they cause including peptic ulcers & gastroduadenal ulcers, chronic Gastritis, and Crohn's Disease.

In yet another group of embodiments, is provided the use of (R)-ornidazole, (S)-ornidazole, and (rac)-ornidazole in a combination product (e.g. a fixed dose combination product) with a beta lactam antibiotic for the prophylaxis and/or treatment of diseases related to *H. pylori* biofilm infection, (including metronidazole resistant *H. pylori* infection).

(R)-ornidazole, (S)-ornidazole, and (rac)-ornidazole are highly active against strains of *H. pylori* (including metronidazole resistant strain of *H. pylori*) which cause clinically relevant cases of peptic ulcers & gastroduadenal ulcers, chronic gastritis, and Crohn's Disease and other antibiotics are active against other causative species of bacteria in these infections. Thus, combination product of (R)-ornidazole, (S)-ornidazole, and (rac)-ornidazole and such other antibiotic(s) is expected to have superior efficacy in the treatment of these indications compared to known actives or the use of these agents alone. The product or combination product can be used as a therapeutic (e.g. fixed dose therapeutic) fixed dose in oral sachet, oral solid, and parental formulations.

In addition, the pharmacologic parameters of (R)-ornidazole, (S)-ornidazole, and (rac)-ornidazole make them appropriate to use in the setting of the treatment of *H. pylori* bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of oral formulations for these *H. pylori* bacterial infections including sachet formulations of powder and or pelletized granules, capsules containing (R)-ornidazole, oral solid tablet formulations, and liquid oral suspension formulations. These include sachet formulations with vehicles for varying absorbencies for delivery to different locations in the gastrointestinal (GI) tract, capsules containing powders or pelletized granules with these properties, and oral solid tablet formulations with different types of slow release properties. These formulations are particularly appropriate for treatment of gram negative anaerobic bacteria like *H. pylori* that are resident in the GI tract, the typical site of infections in the above mentioned indications. In some case, parenteral formulations, such as (R)-ornidazole, (S)-ornidazole, and (rac)-ornidazole in hydrochloride form, are most appropriate for patients in certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of Abdominal and Intra-Abdominal Infections

In one group of embodiments, the present invention provides the use of (R)-ornidazole, (S)-ornidazole, and (rac)-ornidazole in a combination product (e.g. a fixed dose combination product) with a quinolone (including, but not limited to ciprofloxacin, levofloxacin, enoxacin, fleroxacin, & ofloxacin) antibiotic for the prophylaxis and treatment of abdominal and intra-abdominal infections (including severe abdominal and intra-abdominal infections, e.g. peritonitis, intra-abdominal abscess, liver abscess).

In another group of embodiments, are provided formulations (e.g. oral or parenteral formulations) comprising (R)-ornidazole, (S)-ornidazole, and (rac)-ornidazole, alone or in combination with other antibiotics in the quinolone, beta lactam, and macrolide classes, for use in treating abdominal and intra-abdominal infections (including severe abdominal and intra-abdominal infections, e.g. peritonitis, intra-abdominal abscess, liver abscess).

In yet another group of embodiments, is provided the use of (R)-ornidazole, (S)-ornidazole, and (rac)-ornidazole in a combination product (e.g. a fixed dose combination product) with a beta lactam antibiotic for the prophylaxis and treatment of abdominal and intra-abdominal infections (including severe abdominal and intra-abdominal infections, e.g. peritonitis, intra-abdominal abscess, liver abscess).

(R)-ornidazole, (S)-ornidazole, and (rac)-ornidazole are highly active against biofilms of *Bacteroides* species including but not limited to *Bacteroides fragilis, Fusobacterium* species, *Clostridium* species, *Peptococcus* species, *Peptostreptococcus* species, *Eubacterium* species, *Prevotella* species, the bacteria which cause clinically relevant cases of severe abdominal and intra-abdominal infections (including severe abdominal and intra-abdominal infections, e.g. peritonitis, intra-abdominal abscess, liver abscess) and other antibacterial agents are active against other causative species of bacteria in these infections. Thus, combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

In addition, the pharmacologic parameters of (R)-ornidazole, (S)-ornidazole, and (rac)-ornidazole make them appropriate to use in the setting of the treatment the above enumerated bacterial infections and their related indications. ((R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of fixed dose oral formulations for these bacterial infections including sachet formulations of powder and or pelletized granules, capsules containing ((R)-ornidazole, (S)-ornidazole, and (rac)-ornidazole, oral solid tablet formulations, and liquid oral suspension formulations. These include oral sachet, and oral solid tablet formulations with different types of slow release properties. These formulations, as well as fixed dose combination parenteral formulations of these drugs, are particularly appropriate for treatment of severe abdominal and intra-abdominal infections. The disposition of (R)-ornidazole, (S)-ornidazole, and (rac)-ornidazole in the human body is similar for both oral and intravenous dosage forms and the present invention applies to the usage of both of these forms in these settings.

Treatment of Skin Infections

In one group of embodiments, the present invention provides the use of (R)-ornidazole, (S)-ornidazole, and (rac)-ornidazole in a combination product (e.g. a fixed dose combination product) with a quinolone (including, but not limited to ciprofloxacin, levofloxacin, enoxacin, fleroxacin, & ofloxacin) antibiotic for the prophylaxis and/or treatment of complicated and uncomplicated skin infections including, but not limited to, diabetic foot ulcers and surgical wound infections.

In another group of embodiments, are provided formulations (e.g. oral or parenteral formulations) comprising (R)-ornidazole, (S)-ornidazole, and (rac)-ornidazole, alone or in combination with other antibiotics in the quinolone, beta lactam, and macrolide classes, for use in treating skin infections (e.g. complicated and uncomplicated skin infections) including, but not limited to, diabetic foot ulcers and surgical wound infections.

(R)-ornidazole, (S)-ornidazole, and (rac)-ornidazole are highly active against anaerobic bacteria which cause many clinically relevant cases of complicated and uncomplicated skin infections and quinolones are active against other causative species of bacteria in these infections. Thus a combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

In addition, the pharmacologic parameters of ((R)-ornidazole, (S)-ornidazole, and (rac)-ornidazole make them appropriate to use in the setting of bacterial infections related to complicated and uncomplicated skin infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet, and oral solid tablet formulations with different types of slow release properties as well as topical formulations. These formulations are particularly appropriate for treatment of complicated and uncomplicated skin infections. In many of the most severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of Skin Infections in Combination Therapy

In one group of embodiments, the present invention provides the use of (R)-ornidazole, (S)-ornidazole, and (rac)-ornidazole in a combination product (e.g. a fixed dose combination product) with a quinolone (including, but not limited to ciprofloxacin, levofloxacin, enoxacin, fleroxacin, & ofloxacin) antibiotic for the prophylaxis and/or treatment of complicated and uncomplicated skin infections including, but not limited to, diabetic foot ulcers and surgical wound infections.

In another group of embodiments, are provided formulations (e.g. oral or parenteral formulations) comprising (R)-ornidazole, (S)-ornidazole, and (rac)-ornidazole, alone or in combination with other antibiotics in the quinolone, beta lactam, and macrolide classes, for use in treating skin infections (e.g. complicated and uncomplicated skin infections) including, but not limited to, diabetic foot ulcers and surgical wound infections (R)-ornidazole, (S)-ornidazole, and (rac)-ornidazole are highly active against anaerobic bacteria which cause many clinically relevant cases of complicated and uncomplicated skin infections and quinolones are active against other causative species of bacteria in these infections. Thus a combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

In addition, the pharmacologic parameters of (R)-ornidazole, (S)-ornidazole, and (rac)-ornidazole make them appropriate to use in the setting of bacterial infections related to complicated and uncomplicated skin infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet, and oral solid tablet formulations with different types of slow release properties as well as topical formulations. These formulations are particularly appropriate for treatment of complicated and uncomplicated skin infections. In many of the most severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of ((R)-ornidazole, (S)-ornidazole, and (rac)-ornidazole in the human body is similar for both oral and intravenous dosage forms and the present invention applies to the usage of both of these forms in these settings.

Treatment of Rosacea

In some embodiments of the present invention, there are provided formulations (e.g. topical formulations) comprising (R)-ornidazole, (S)-ornidazole, and (rac)-ornidazole for the treatment of rosacea. In one embodiment (R)-ornidazole, (S)-ornidazole, and (rac)-ornidazole are administered topically for the treatment of rosacea. This allows the use of higher dosages and concentrations than can be administered systemically. Appropriate topical formulations include gels, creams, and lotions for the treatment of either localised sites or larger surface areas.

Rosacea is a chronic condition characterized by facial erythema (redness). Pimples are sometimes included as part of the definition. Rosacea affects both sexes, but is almost three times more common in women. It has a peak age of onset between 30 and 60. Patients with rosacea have elevated levels of the peptide cathelicidin and elevated levels of stratum corneum tryptic enzymes (SCTEs). (R)-ornidazole, (S)-ornidazole, and (rac)-ornidazole in roseacea works, in part, because it inhibits some SCTEs as well as intestinal bacteria (small intestinal bacterial overgrowth [SIBO]) which play a role in causing the disease. *Bacillus oleronius* may also be implicated in rosacea and accordingly the inhibition or eradication of this organism by administering, suitably topically, a therapeutically effective dose of (R)-ornidazole, (S)-ornidazole, and (rac)-ornidazole may be beneficial in the treatment of rosacea. Accordingly in a further embodiment there is provided (R)-ornidazole, (S)-ornidazole, and (rac)-ornidazole for use in the treatment of rosacea associated with *Bacillus oleronius*.

While the exact mechanism of action and pharmacodynamics of both topical and systemic oral treatment with (R)-ornidazole, (S)-ornidazole, and (rac)-ornidazole in roseacea is unknown, the result of treatment is efficacious.

Treatment of Fungating Tumors

In some embodiments of the invention, there are provided formulations (e.g. topical and systemic, including both oral and intravenous formulations) comprising (R)-ornidazole, (S)-ornidazole, and (rac)-ornidazole for the treatment of fungating tumors or lesions.

A fungating tumor or lesion is a type of skin lesion that is marked by ulcerations (breaks on the skin or surface of an organ) and necrosis (death of living tissue) and that usually has a bad smell, often associated with the presence of gram negative anaerobic bacteria. This kind of lesion may occur in many types of cancer, including breast cancer, melanoma, and squamous cell carcinoma, and especially in advanced disease.

(R)-ornidazole, (S)-ornidazole, and (rac)-ornidazole treats the condition through a variety of mechanisms, including, but not limited to, eradicating the gram negative anaerobic bacteria in the tissue.

Treatment of Decubitus Ulcers

In some embodiments of the invention, there are provided formulations (e.g. topical and systemic, including both oral and intravenous formulations) comprising (R)-ornidazole, (S)-ornidazole, and (rac)-ornidazole, either alone or in combination with other antibiotics, for the treatment of decubitus ulcers (bed sores).

Bedsores, more properly known as pressure ulcers or decubitus ulcers, are lesions caused by many factors such as: unrelieved pressure; friction; humidity; shearing forces; temperature; age; continence and medication; to any part of the body, especially portions over bony or cartilaginous areas such as sacrum, elbows, knees, and ankles. Although often prevented and treatable if found early, they can be very difficult to prevent in frail elderly patients, wheelchair users (especially where spinal injury is involved) and terminally ill patients. Bedsores are often fatal—even under the auspices of medical care—and are one of the leading iatrogenic causes of death reported in developed countries, second only to adverse drug reactions. The primary cure and treatment is to remove the pressure by turning the patient regularly. Frequently, tissue damaged through decubitus ulcers becomes infected with a variety of gram negative bacteria which both complicates the treatment of the ulcers and can pose life threatening consequences if the patient becomes septic.

Treatment with (R)-ornidazole, (S)-ornidazole, and (rac)-ornidazole, in topical, oral systemic and intravenous formulations, either alone or in combination with other antibiotics, can eradicate the causative pathogens in these infections.

Treatment of *Borrelia* (e.g. *Borrelia burgdorferi*) Infections e.g. Lyme Disease In one group of embodiments, the present invention provides therapeutic uses of (R)-ornidazole, (S)-ornidazole, and (rac)-ornidazole in a combination product (e.g. a fixed dose combination product) with a macrolide (including, but not limited to erythromycin, clarithromycin, & azithromycin) or tetracycline antibiotic for the treatment of Lyme Disease (including bacterial infections caused by biofilms of *Borrelia burgdorferi* and other instances of Lyme disease caused by other *Borrelia*).

In another group of embodiments, the present invention provides therapeutic uses of (R)-ornidazole in different oral, topical and parenteral formulations for the treatment of bacterial infections including Lyme Disease (e.g. that caused by *Borrelia burgdorferi*). (R)-ornidazole, (S)-ornidazole, and (rac)-ornidazole is effective in combination with one or more antibiotics in the beta lactam (penicillin & cephalosporin), tetracycline, and macrolide classes of antibiotics where there is a likelihood of the presence of the biofilm and cystic form of the bacteria as well as other forms highly sensitive to these other classes of drugs.

Lyme Disease incidence has increased dramatically in the United States to the point that the disease has become an important public health problem. Today, Lyme Disease is the most prevalent tick-borne illness in the United States. *Borrelia burgdorferi* consists of three strains sensitive to (R)-ornidazole, (S)-ornidazole, and (rac)-ornidazole, collectively known as *Borrelia burgdorferi* sensu lato. These genospecies are *Borrelia burgdorferi* sensu strict, *Borrelia garinii*, and *Borrelia afzelii*. In addition the genospecies *Borrelia valaisiana* is also a suspected pathogenic strain implicated in Lyme Disease (Lyme borreliosis in Europe influences of climate and climate change, epidemiology, ecology and adaptation measures; Elisabet Lindgren and Thomas G. T. Jaenson; WHO Report on project number (EVK2-2000-00070)). The *Borrelia valaisiana* strain may also be susceptible to treatment with (R)-ornidazole, (S)-ornidazole, and (rac)-ornidazole).

(R)-ornidazole, (S)-ornidazole, and (rac)-ornidazole are highly active against the biofilm and cystic form of *Borrelia burgdorferi*, unlike many other antibiotics, and macrolides and β-lactam antibiotics are highly active against the other forms of *Borrelia burgdorferi*, (e.g. the corkscrew form) Thus, the combination products of the invention will be have superior efficacy in these mixed form infection settings of Lyme Disease. (R)-ornidazole, (S)-ornidazole, and (rac)-ornidazole can therefore be used as an antibiotic to treat these infections either in a fixed dose tetracycline or macrolide combination that is active against *Borrelia burgdorferi* sensu lato spirochete bacteria or a single agent in sensitive strains.

In addition, the pharmacologic parameters of (R)-ornidazole, (S)-ornidazole, and (rac)-ornidazole make them appropriate to use in the setting of the treatment of *Borrelia burgdorferi* bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole has an elimination half life that enables more convenient dosing of oral formulations for these *Borrelia burgdorferi* bacterial infections including sachet formulations of powder and or pelletized granules, capsules containing (R)-ornidazole, (S)-ornidazole, and (rac)-ornidazole, oral solid tablet formulations, and liquid oral suspension formulations. These include sachet formulations with vehicles for varying absorbencies for delivery to different locations in the gastro-intestinal (GI) tract, capsules containing powders or pelletized granules with these properties, and oral solid tablet formulations with different types of slow release properties. These formulations are particularly appropriate for treatment of gram negative bacteria like *Borrelia burgdorferi*. In some case, parenteral formulations, such as (R)-ornidazole, (S)-ornidazole, and (rac)-ornidazole in hydrochloride form, are most appropriate for patients in certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of *Burkholderia* infections (R)-ornidazole, (S)-ornidazole, and (rac)-ornidazole, or pharmaceutically acceptable salts or esters thereof, for use in the treatment of Glanders and Melioidosis infections wherein the Glanders and Melioidosis infections are caused by biofilms of *Burkholderia mallei* or *Burholderia pseudomallei* and at least some of the bacteria are present in an aneroebic configuration.

In another embodiment, the (R)-ornidazole, (S)-ornidazole, and (rac)-ornidazole are for use in combination to treat *Burkholderia* infections with one or more antibiotics, the antibiotics being selected from β-lactam antibiotics (including amoxiclav), tetracycline antibiotics, penem antibiotics, quinolone antibiotics and macrolide antibiotics.

Treatment of *Coxiella* Infections (R)-ornidazole, (S)-ornidazole, and (rac)-ornidazole, or pharmaceutically acceptable salts or esters thereof, for use in the treatment of Q-fever infections wherein the Q-fever infections are caused by *Coxiella burnetii* and at least some of the bacteria are present in an aneroebic configuration.

In another embodiment, (R)-ornidazole, (S)-ornidazole, and (rac)-ornidazole in *Coxiella* and Q-fever infections is for use in combination with one or more antibiotics, the antibiotics being selected from β-lactam antibiotics, tetracycline antibiotics, penem antibiotics, quinolone antibiotics and macrolide antibiotics.

*Coxiella burnetii* is an obligate intracellular bacterial pathogen, and is the causative agent of Q fever. The genus *Coxiella* is morphologically similar to *Rickettsia*, but with a variety of genetic and physiological differences. *C. burnetii* is a small Gram-negative bacterium that is highly resistant to environmental stresses such as high temperature, osmotic pressure, and ultraviolet light. These characteristics are attributed to a small cell variant form of the organism that is part of a biphasic developmental cycle, including a more metabolically and replicatively active large cell variant form.

Treatment of Lung Infections

In one group of embodiments, they are provided formulations (e.g. oral or parenteral formulations) comprising (R)-ornidazole, (S)-ornidazole, and (rac)-ornidazole, alone or in combination with other antibiotics including, but not limited to, those in the quinolone, beta lactam, and macrolide classes, for use in treating lung infections including, but not limited to, emphysema, pneumonia & aspiration pneumonia, Lemmiere's Syndrome and lung abscess.

Because (R)-ornidazole, (S)-ornidazole, and (rac)-ornidazole are highly active against anaerobic bacteria which cause clinically relevant cases of pulmonary related infections, it will be used as therapeutic in oral sachet, oral solid, and parental formulations in these settings. (R)-ornidazole, (S)-ornidazole, and (rac)-ornidazole can therefore be used as an antibiotic to treat these infections either alone or in combination with other antibiotics that are active against these gram negative anaerobe bacteria including, but not limited to quinolone, beta lactam, and macrolide classes of antibiotics.

In addition, the pharmacologic parameters of (R)-ornidazole, (S)-ornidazole, and (rac)-ornidazole make them appropriate to use in the setting of the treatment of the above enumerated gram negative bacterial infections related to pulmonary associated infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of oral formulations for these gram negative bacterial infections including sachet formulations of powder and or pelletized granules, capsules containing ((R)-ornidazole, (S)-ornidazole, and (rac)-ornidazole, oral solid tablet formulations, and liquid oral suspension formulations. These include oral sachet and oral solid tablet formulations with different types of slow release properties. These formulations are particularly appropriate for treatment of the above enumerated gram negative anaerobic bacteria. In many of these severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of Central Nervous System Infections

In one group of embodiments, are provided formulations (e.g. oral or parenteral formulations) comprising (R)-ornidazole, (S)-ornidazole, and (rac)-ornidazole, alone or in combination with other antibiotics including, but not limited to, those in the quinolone, beta lactam, and macrolide classes, for use in treating central nervous system related infections including, but not limited to, meningitis and brain abscesses and infection related conditions including autism and Parkinson's Disease.

(R)-ornidazole, (S)-ornidazole, and (rac)-ornidazole are highly active against anaerobic bacteria which cause clinically relevant cases of central nervous system related infections, it will be used as therapeutic in oral sachet, oral solid, and parental formulations in these settings. ((R)-ornidazole, (S)-ornidazole, and (rac)-ornidazole can therefore be used as an antibiotic to treat these infections either alone or in combination with other antibiotics that are active against these gram negative anaerobe bacteria including, but not limited to quinolone, beta lactam, and macrolide classes of antibiotics.

In addition, the pharmacologic parameters of (R)-ornidazole, (S)-ornidazole, and (rac)-ornidazole make them appropriate to use in the setting of the treatment of the above enumerated gram negative bacterial infections related to central nervous system infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of oral formulations for these gram negative bacterial infections including sachet formulations of powder and or pelletized granules, capsules containing (R)-ornidazole, (S)-ornidazole, and (rac)-ornidazole, oral solid tablet formulations, and liquid oral suspension formulations. These include sachet, oral solid tablet formulations with different types of slow release properties, and vaginal suppository/topical formulations. These formulations are particularly appropriate for treatment of the above enumerated gram negative anaerobic bacteria. In many of these severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Autism is a highly variable neurodevelopmental disorder that first appears during infancy or childhood, and generally follows a steady course without remission. Overt symptoms gradually begin after the age of six months, become established by age two or three years, and tend to continue through adulthood, although often in more muted form. It is distinguished not by a single symptom, but by a characteristic triad of symptoms: impairments in social interaction; impairments in communication; and restricted interests and repetitive behavior. Atypical eating is common and is related to dysbiosis of GI microbiota. This unusual eating behavior occurs in about three-quarters of children with ASD. Autism symptoms in patients have been mitigated through antibiotic manipulation of microbiota in the GI system with vancomycin and will respond better to (R)-ornidazole, (S)-ornidazole, and (rac)-ornidazole given the range of bacteria affected and shifted in the beta dimension of compositional diversity.

Parkinson's disease is a degenerative disorder of the central nervous system. The motor symptoms of Parkinson's disease result from the death of dopamine-generating cells in the substantia nigra, a region of the midbrain; the cause of this cell death is unknown. Early in the course of the disease, the most obvious symptoms are movement-related; these include shaking, rigidity, slowness of movement and difficulty with walking and gait. Atypical microbiota enterotypes in Parkinson's disease is related to dysbiosis of GI microbiota. Parkinson's disease symptoms in patients can be mitigated through antibiotic manipulation of microbiota in the GI system with ((R)-ornidazole, (S)-ornidazole, and (rac)-ornidazole given the range of bacteria affected and shifted in the beta dimension of compositional diversity.

Treatment Blood Infections

In one group of embodiments, are provided formulations (e.g. oral or parenteral formulations) comprising (R)-ornidazole, (S)-ornidazole, and (rac)-ornidazole, alone or in combination with other antibiotics including, but not limited to, those in the quinolone, beta lactam, penem and macrolide classes, for use in treating blood infections including, but not limited to, bacteremia and septicemia.

Because (R)-ornidazole, (S)-ornidazole, and (rac)-ornidazole are highly active against anaerobic bacteria which cause clinically relevant cases of blood stream related infections, it can be used as therapeutic in oral sachet, oral solid, and parental formulations in these settings. (R)-ornidazole, (S)-ornidazole, and (rac)-ornidazole can therefore be used as an antibiotic to treat these infections either alone or in combination with other antibiotics that are active against these gram negative anaerobe bacteria including, but not limited to quinolone, beta lactam, penem, and macrolide classes of antibiotics.

In addition, the pharmacologic parameters of (R)-ornidazole, (S)-ornidazole, and (rac)-ornidazole make them appropriate to use in the setting of the treatment of the above enumerated gram negative bacterial infections related to central nervous system infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of oral formulations for these gram negative bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet and oral solid tablet formulations with different types of slow release properties. These formulations are particularly appropriate for treatment of the above enumerated gram negative anaerobic bacteria. In many of these severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of Bone and Joint Infections

In one group of embodiments, there are provided formulations (e.g. oral or parenteral formulations) comprising (R)-ornidazole, (S)-ornidazole, and (rac)-ornidazole, alone or in combination with other antibiotics including, but not limited to, those in the tetracycline, quinolone, beta lactam, penem and macrolide classes, for use in treating bone and joint related infections.

Because (R)-ornidazole, (S)-ornidazole, and (rac)-ornidazole are highly active against anaerobic bacteria which cause clinically relevant cases of bone and joint related infections, it can be used as therapeutic in oral sachet, oral solid, and parental formulations in these settings. (R)-ornidazole, (S)-ornidazole, and (rac)-ornidazole can therefore be used as an antibiotic to treat these infections either alone or in combination with other antibiotics that are active against these gram negative anaerobe bacteria including, but not limited to quinolone, beta lactam, penem, and macrolide classes of antibiotics.

In addition, the pharmacologic parameters of (R)-ornidazole, (S)-ornidazole, and (rac)-ornidazole make it appropriate to use in the setting of the treatment of the above enumerated gram negative bacterial infections related to central nervous system infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of oral formulations for these gram negative bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet and oral solid tablet formulations with different types of slow release properties. These formulations are particularly appropriate for treatment of the above enumerated gram negative anaerobic bacteria. In many of these severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of Heart Infections

In one group of embodiments, are provided formulations (e.g. oral or parenteral formulations) comprising (R)-ornidazole, (S)-ornidazole, and (rac)-ornidazole, alone or in combination with other antibiotics including, but not limited to, those in the quinolone, beta lactam, penem, and macrolide classes, for use in treating heart infections including but not limited to endocarditis.

Because (R)-ornidazole, (S)-ornidazole, and (rac)-ornidazole are highly active against anaerobic bacteria which cause clinically relevant cases of cause cardiac related infections, it can be used as therapeutic in oral sachet, oral solid, and parental formulations in these settings. (R)-ornidazole, (S)-ornidazole, and (rac)-ornidazole can therefore be used as an antibiotic to treat these infections either alone or in combination with other antibiotics that are active against these gram negative anaerobe bacteria including, but not limited to quinolone, beta lactam, penem, and macrolide classes of antibiotics.

In addition, the pharmacologic parameters of (R)-ornidazole, (S)-ornidazole, and (rac)-ornidazole make them appropriate to use in the setting of the treatment of the above enumerated gram negative bacterial infections related to central nervous system infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of oral formulations for these gram negative bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet and oral solid tablet formulations with different types of slow release properties. These formulations are particularly appropriate for treatment of the above enumerated gram negative anaerobic bacteria. In many of these severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Treatment of Venereal Disease or Sexually Transmitted Disease (STD)

Syphilis is a sexually transmitted infection caused by the spirochete bacterium *Treponema pallidum* subspecies *pallidum*. The primary route of transmission is through sexual contact; it may also be transmitted from mother to fetus during pregnancy or at birth, resulting in congenital syphilis. Other human diseases caused by related *Treponemapaffidum* include yaws (subspecies *pertenue*), pinta (subspecies *carateum*), and bejel (subspecies *endemicum*).

Because (R)-ornidazole, (S)-ornidazole, and (rac)-ornidazole are highly active against biofilms of anaerobic bacteria which cause clinically relevant cases of syphilis and yaws, it can be used as therapeutic in oral sachet, oral solid, and parental formulations in these settings. (R)-ornidazole, (S)-ornidazole, and (rac)-ornidazole can therefore be used as an antibiotic to treat these infections either alone or in combination with other antibiotics that are active against these gram negative anaerobe bacteria including, but not limited to quinolone, beta lactam, penem, and macrolide classes of antibiotics.

In addition, the pharmacologic parameters of (R)-ornidazole, (S)-ornidazole, and (rac)-ornidazole make them appropriate to use in the setting of the treatment of the above enumerated gram negative bacterial infections related to syphilis and yaws infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of oral formulations for these gram negative bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet and oral solid tablet formulations with different types of slow release properties. These formulations are particularly appropriate for treatment of the above enumerated gram negative anaerobic bacteria. In many of these severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Bacterial urethritis is inflammation of the urethra caused by bacteria. The urethra is the tube that carries urine from the bladder to outside the body. Pain with urination is the main symptom of bacterial urethritis. Bacterial urethritis is due to infection by bacteria through sexual contact. It can be cured with (R)-ornidazole, (S)-ornidazole, and (rac)-ornidazole.

Prevention of Sexually Transmitted Disease (STD) transmission

A key favorable condition for transmission of sexually transmitted diseases (STDs), including, but not limited to, human immunodeficiency virus (HIV), herpes simplex virus (HSV), hepatitis C virus (HCV), hepatitis B virus (HBV), human papilloma virus (HPV), gonorrhea, and syphilis, is changes that occur in the normal balance between organisms in the vagina when the number of protective bacteria like *Lactobacilli* decrease. This often occurs in a situation of bacterial vaginosis. Hence, bacterial vaginosis, by reducing the presence of lactic acid producing *Lactobacilli* and the breakdown of the vaginal mucosal barrier by other overgrowing bacterial species such as *Bacteroides* species and *Gardnerella* species, predisposes these women to getting the above delineated STDs. Because the underlying cause of the breakdown of the physical vaginal mucosal barrier and its pH chemical barrier from lactic acid is a bacterial infection that creates a suitable environment for pathogenic bacteria overgrowth, the treatment of bacterial vaginitis with an effective antibacterial agent will diminish the transmission of the these STD infections. In cases with multiple types of bacteria being overgrown, ie, bacterial vaginosis or in an overgrowth of vaginal protozoal pathogens (trichomoniasis), it has been shown that infections are a major risk factors in HIV transmission as well as the transmission of the other STDs listed above. Treatment with a combination of an antibiotic and anti-protozoal agent will prevent the sexual transmission of these STDs by infected males or females to susceptible females with either symptomatic or asymptomatic bacterial vaginitis or vaginosis by eliminating the overgrowth of pathogen bacteria or protozoa and the re-establishment of the natural predominant commensal *Lactobacilli* flora.

In one group of embodiments, the present invention provides the use of (R)-ornidazole, (S)-ornidazole, and (rac)-ornidazole, (e.g. in either an oral or vaginal formulation), in combination with antifungal drugs active against *Candida albicans* (including, but not limited to fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin) for the prevention of STD transmission related to bacterial vaginosis and/or trichmoniasis and/or vaginal candidiasis. The antifungal drug may be in the form of a vaginal topical or systemic (e.g. oral) formulation. A single dose treatment with an oral sachet formulation of (R)-ornidazole, (S)-ornidazole, and (rac)-ornidazole may be the only administration of (R)-ornidazole, (S)-ornidazole, and (rac)-ornidazole during the entire treatment.

In the above section, and throughout this specification, the term 'prevention of STD transmission' means eliminating or reducing the risk of said transmission.

If present, the single dose treatment oral sachet formulation and the vaginal topical or systemic (e.g. oral) formulation of the antifungal drug may be provided in the form of a kit.

Treatment of Urinary Tract Infections

In one group of embodiments, the present invention provides the use of (R)-ornidazole, (S)-ornidazole, and (rac)-ornidazole in a combination product (e.g. a fixed dose combination product) with a quinolone (including, but not limited to ciprofloxacin, levofloxacin, enoxacin, fleroxacin, & ofloxacin) antibiotic for the prophylaxis and treatment of urinary tract infections (e.g. complicated and uncomplicated urinary tract infections).

In another group of embodiments, are provided formulations (e.g. oral or parenteral formulations) comprising (R)-ornidazole, (S)-ornidazole, and (rac)-ornidazole, alone or in combination with other antibiotics in the quinolone, beta lactam, and macrolide classes, for use in treating urinary tract infections (e.g. complicated and uncomplicated urinary tract infections).

(R)-ornidazole, (S)-ornidazole, and (rac)-ornidazole are highly active against anaerobic bacteria which cause many clinically relevant cases of complicated and uncomplicated urinary tract infections and other antibiotics are active against other causative species of bacteria in these infections. Thus combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

In addition, the pharmacologic parameters of (R)-ornidazole, (S)-ornidazole, and (rac)-ornidazole make them appropriate to use in the setting of bacterial infections related to complicated and uncomplicated urinary tract infections. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include sachet, and oral solid tablet formulations with different types of slow release properties. These formulations are particularly appropriate for treatment of infections caused by bacteria resident in the urinary tract. In many of the most severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole in the human body is similar for both oral and intravenous dosage forms and the present invention applies to the usage of both of these forms in these settings.

Treatment of Pelvic Inflammatory Disease and Endometritis

In one group of embodiments, the present invention provides the use of (R)-ornidazole, (S)-ornidazole, and (rac)-ornidazole in a combination product (e.g. a fixed dose combination product) with a quinolone (including, but not limited to ciprofloxacin, levofloxacin, enoxacin, fleroxacin, & ofloxacin) antibiotic for the prophylaxis and treatment of pelvic inflammatory disease and endometritis.

(R)-ornidazole, (S)-ornidazole, and (rac)-ornidazole are highly active against gram negative anaerobic bacteria which can contribute to causing clinically relevant cases of pelvic inflammatory disease and endometritis, and quinolones are active against other causative species of bacteria in pelvic inflammatory disease and endometritis. Thus, combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

In addition, the pharmacologic parameters of (R)-ornidazole, (S)-ornidazole, and (rac)-ornidazole make it appropriate to use in the setting of the treatment the above enumerated bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet, and oral solid tablet formulations with different types of slow release properties.

Treatment of Endometritis and Endomyometritis

In one group of embodiments, is provided the use of (R)-ornidazole, (S)-ornidazole, and (rac)-ornidazole (e.g. as an oral, vaginal topical or parenteral formulation) for the treatment of endometritis.

Endometritis refers to inflammation of the endometrium, the inner lining of the uterus. Pathologists have traditionally classified endometritis as either acute or chronic: acute endometritis is characterized by the presence of microabscesses or neutrophils within the endometrial glands, while chronic endometritis is distinguished by variable numbers of plasma cells within the endometrial stroma. The most common cause of endometritis is infection. Symptoms include lower abdominal pain, fever and abnormal vaginal bleeding or discharge. The present invention is for the treatment of endometritis with (R)-ornidazole, (S)-ornidazole, and (rac)-ornidazole in different parenteral, oral and vaginal formulations (including topical vaginal and dissolvable vaginal ampoules), also including a single dose treatment of an oral sachet formulation for the entire treatment for a course of therapy. This treatment eradicates strains of the causative bacterial pathogens that are both sensitive and resistant to other antibacterial agents and in women who are both symptomatic and asymptomatic with endometritis.

In one group of embodiments, the present invention provides the use of (R)-ornidazole, (S)-ornidazole, and (rac)-ornidazole in a combination product (e.g. a fixed dose combination product) with a quinolone (including, but not limited to ciprofloxacin, levofloxacin, enoxacin, fleroxacin, & ofloxacin) antibiotic for the prophylaxis and treatment of endometritis.

(R)-ornidazole, (S)-ornidazole, and (rac)-ornidazole are highly active against gram negative anaerobic bacteria which can contribute to causing clinically relevant cases of endometritis, and quinolones are active against other causative species of bacteria in pelvic inflammatory disease and endometritis. Thus, combination product of (R)-ornidazole, (S)-ornidazole, and (rac)-ornidazole and such other antibiotic(s) is expected to have superior efficacy in the treatment of these indications compared to the use of these agents alone. The combination product can be used as a fixed dose therapeutic in oral sachet, oral solid, and parental formulations.

In addition, the pharmacologic parameters of (R)-ornidazole, (S)-ornidazole, and (rac)-ornidazole make them appropriate to use in the setting of the treatment the above enumerated bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet, and oral solid tablet formulations with different types of slow release properties.

In one group of embodiments, is provided the use of (R)-ornidazole, (S)-ornidazole, and (rac)-ornidazole (e.g. as an oral, vaginal topical or parenteral formulation) for the treatment of endomyometritis.

The term "endomyometritis" is sometimes used to specify inflammation of the endometrium and the myometrium. The most common cause of endomyometritis is infection. Symptoms include lower abdominal pain, fever and abnormal vaginal bleeding or discharge. The present invention is for the treatment of endomyometritis with rac-ornidazole in different parenteral, oral and vaginal formulations (including topical vaginal and dissolvable vaginal ampoules), also including a single dose treatment of an oral sachet formulation for the entire treatment for a course of therapy. This treatment eradicates strains of the causative bacterial pathogens that are both sensitive and resistant to other antibacterial agents and in women who are both symptomatic and asymptomatic with endomyometritis.

Endometritis

In one group of embodiments, is provided the use of (R)-ornidazole, (S)-ornidazole, and (rac)-ornidazole (e.g. as a oral, vaginal topical or parenteral formulation) for the treatment of endometritis.

Endometritis refers to inflammation of the endometrium, the inner lining of the uterus. Pathologists have traditionally classified endometritis as either acute or chronic: acute endometritis is characterized by the presence of microabscesses or neutrophils within the endometrial glands, while chronic endometritis is distinguished by variable numbers of plasma cells within the endometrial stroma. The most common cause of endometritis is infection. Symptoms include lower abdominal pain, fever and abnormal vaginal bleeding or discharge. The present invention is for the treatment of endometritis with the (R)-ornidazole, (S)-ornidazole, and (rac)-ornidazole in different parenteral, oral and vaginal formulations (including topical vaginal and dissolvable vaginal ampoules), also including a single dose treatment of an oral sachet formulation for the entire treatment for a course of therapy. This treatment eradicates strains of the causative bacterial pathogens that are both sensitive and resistant to other antibacterial agents and in women who are both symptomatic and asymptomatic with endometritis.

Endomyometritis

In one group of embodiments, is provided the use of (R)-ornidazole, (S)-ornidazole, and (rac)-ornidazole (e.g. as an oral, vaginal topical or parenteral formulation) for the treatment of endometritis.

The term "endomyometritis" is sometimes used to specify inflammation of the endometrium and the myometrium. The most common cause of endomyometritis is infection. Symptoms include lower abdominal pain, fever and abnormal vaginal bleeding or discharge. The present invention is for the treatment of endomyometritis with (R)-ornidazole, (S)-ornidazole, and (rac)-ornidazole in different parenteral, oral and vaginal formulations (including topical vaginal and dissolvable vaginal ampoules), also including a single dose treatment of an oral sachet formulation for the entire treatment for a course of therapy. This treatment eradicates strains of the causative bacterial pathogens that are both sensitive and resistant to other antibacterial agents and in women who are both symptomatic and asymptomatic with endomyometritis.

Tubo-Ovarian Abscess

In one group of embodiments, is provided the use of (R)-ornidazole, (S)-ornidazole, and (rac)-ornidazole (e.g. as an oral, vaginal topical or parenteral formulation) for the treatment of a tubo-ovarian abscess.

A tubo-ovarian abscess (TOA) is an inflammatory mass involving the fallopian tube, ovary, and, occasionally, other adjacent pelvic organs (e.g., bowel, bladder). These abscesses are found most commonly in reproductive age women and typically result from upper genital tract infection.

Tubo-ovarian abscess is a serious and potentially life-threatening condition. Aggressive medical and/or surgical therapy is required and rupture of an abscess may result in sepsis. Prior to the advent of broad-spectrum antibiotics and modern surgical practice, the mortality rate associated with tubo-ovarian abscess was approximately 50 percent or higher.

The present invention is for the treatment of TOA with the (R)-ornidazole, (S)-ornidazole, and (rac)-ornidazole in different parenteral, oral and vaginal formulations (including topical vaginal and dissolvable vaginal ampoules), also including a single dose treatment of an oral sachet formulation for the entire treatment for a course of therapy. This treatment eradicates strains of the causative bacterial pathogens that are both sensitive and resistant to other antibacterial agents and in women who have TOA.

Postsurgical Vaginal Cuff Infection

In one group of embodiments, is provided the use of (R)-ornidazole, (S)-ornidazole, and (rac)-ornidazole (e.g. as an oral, vaginal topical or parenteral formulation) for the treatment of vaginal cuff infection (e.g. post-surgical vaginal cuff infection).

Total abdominal hysterectomy is the most common procedure for removing the uterus. Infection of the vaginal cuff is commonly reported as a complication of this surgical procedure. The causative pathogens for vaginal cuff infections are the same pathogens found in bacterial vaginosis.

The present invention is for the treatment of postsurgical vaginal cuff infection with (R)-ornidazole, (S)-ornidazole, and (rac)-ornidazole in different parenteral, oral and vaginal formulations (including topical vaginal and dissolvable vaginal ampoules), also including a single dose treatment of an oral sachet formulation for the entire treatment for a course of therapy. This treatment eradicates strains of the causative bacterial pathogens that are both sensitive and resistant to other antibacterial agents and in women who have postsurgical vaginal cuff infections.

In addition, the pharmacologic parameters of (R)-ornidazole, (S)-ornidazole, and (rac)-ornidazole make them appropriate to use in the setting of the treatment the above enumerated bacterial infections and their related indications. (R)-ornidazole, (S)-ornidazole, and (rac)-ornidazole are rapidly absorbed after oral administration and have a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of fixed dose oral formulations for these bacterial infections including sachet formulations of powder and or pelletized granules, capsules containing (R)-ornidazole, (S)-ornidazole, and (rac)-ornidazole, oral solid tablet formulations, and liquid oral suspension formulations. These include oral sachet, and oral solid tablet formulations with different types of slow release properties.

Treatment of Vulvovaginitis

Vulvovaginitis is an inflammation of the vagina and or vulva. It can result in discharge, itching and pain. The three main causes of vulvovaginitis are bacterial vaginosis (BV), vaginal candidiasis, and trichomoniasis. A woman may have any combination of vaginal infections at one time. (R)-ornidazole, (S)-ornidazole, and (rac)-ornidazole are effective alone in treating bacterial vaginosis and trichmoniasis and can be used in combination (e.g. a fixed dose combination) with an antifungal drug to prevent bacterial or protozoal super-infection with mixed infections of fungal pathogens, bacterial pathogens, and protozoal pathogens. The symptoms that arise vary with the infection, although there are general symptoms that all vaginitis infections have and it must be noted that infected women may also be asymptomatic. The present invention treats both symptomatic and asymptomatic infections arising from strains of bacteria that cause bacterial vaginosis as well as protozoa causing trichmoniasis, and the fungi that cause vaginal candidiasis.

In one group of embodiments, the present invention provides the use of (R)-ornidazole, (S)-ornidazole, and (rac)-ornidazole, (e.g. in either an oral or vaginal formulation), in combination with antifungal drugs active against *Candida albicans* (including, but not limited to fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin) for the treatment of vulvovaginitis. The antifungal drug may be in the form of a vaginal topical or systemic (e.g. oral) formulation. A single dose treatment with an oral sachet formulation of (R)-ornidazole, (S)-ornidazole, and (rac)-ornidazole may be the only administration of (R)-ornidazole, (S)-ornidazole, and (rac)-ornidazole for the entire treatment.

If present, the single dose treatment oral sachet formulation and the vaginal topical or systemic (e.g. oral) formulation of the antifungal drug may be provided in the form of a kit.

This treatment is effective for strains of the causative bacterial, fungal, and protozoal pathogens that are both sensitive and resistant to other antibacterial, anti-protozoal and anti-fungal agents. In many cases the bacterial, protozoal, and fungal infections are either mixed or induce each other by altering the normal flora of the vagina. The present invention can allow more convenient empiric treatment as well as treatment when the presence of both fungal and bacterial or protozoal pathogens has been demonstrated. This can prevent secondary super-infections, reduce morbidity and medical expense, and speed recovery. The fixed doses combination drugs have the necessary spectrum of activity to eradicate common causative bacterial, protozoal and fungal pathogens together for concurrent treatment and also will have formulations appropriate to treatment at either the vaginal site of infection, systemic infection, or both.

Treatment of Bacterial Vaginosis

Bacterial vaginosis (BV) is a disease of the vagina caused by bacterial overgrowth of normally predominant lactic acid and hydrogen peroxide producing *Lactobacilli* bacteria (*Lactobacilli* species) by biofilms of other species of bacteria including, but not limited to, *Gardnerella vaginalis*, *Bacteroides* species, *Prevotella* species, and *Mobiluncus* species. In clinical practice BV is diagnosed using the Amsel criteria:

1. Thin, white, yellow, homogeneous discharge
2. Clue cells on microscopy
3. pH of vaginal fluid >4.5
4. Release of a fishy odor on adding alkali—10% potassium hydroxide (KOH) solution.

At least three of the four criteria should be present for a confirmed diagnosis. An alternative is to use a Gram-stained vaginal smear, with the Nugent criteria. The standards for research are the Nugent Criteria. In this scale, a score of 0-10 is generated from combining three other scores. The scores are as follows:

0-3 is considered negative for BV
4-6 is considered intermediate
7+ is considered indicative of BV.

In one group of embodiments, the present invention provides the use of (R)-ornidazole, (S)-ornidazole, and (rac)-ornidazole, (e.g. in either an oral or vaginal formulation), in combination with antifungal drugs active against *Candida albicans* (including, but not limited to fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin) for the treatment of bacterial vaginosis or infections which are suspected to be due at least in part to bacterial vaginitis. The antifungal drug may be in the form of a vaginal topical or systemic (e.g. oral) formulation. A single dose treatment with an oral sachet formulation of (R)-ornidazole, (S)- ornidazole, and (rac)-ornidazole may be the only administration of (R)-ornidazole, (S)-ornidazole, and (rac)-ornidazole for the entire treatment.

(R)-ornidazole, (S)-ornidazole, and (rac)-ornidazole do not effect the beneficial *Lactobacilli* species present in the vagina.

If present, the single dose treatment oral sachet formulation and the vaginal topical or systemic (e.g. oral) formulation of the antifungal drug may be provided in the form of a kit.

This treatment is for strains of the causative bacterial pathogens that are both sensitive and resistant to other antibacterial agents. In many cases the bacterial infection is either mixed with other protozoal or fungal infections or these infections induce each other by altering the normal flora of the vagina. The present invention can allow more convenient empiric treatment as well as treatment when the presence of both fungal and bacterial or protozoal pathogens has been demonstrated. This can prevent secondary super-infections, reduce morbidity and medical expense, and speed recovery. The fixed doses combination drugs have the necessary spectrum of activity to eradicate common causative bacterial, protozoal and fungal pathogens together for concurrent treatment and also will have formulations appropriate to treatment at either the vaginal site of infection, systemic infection, or both.

Treatment of Trichomoniasis

Trichomoniasis, sometimes referred to as "trich" is a sexually transmitted infection. The disease is caused by the single-celled protozoan parasite *Trichomonas vaginalis* producing mechanical stress on host cells and then ingesting cell fragments after cell death. Trichomoniasis is primarily an infection of the urogenital tract; the most common site of infection is the urethra and the vagina in women. Trichomoniasis is also associated with increased risk of transmission of HIV.

In one group of embodiments, the present invention provides the use of (R)-ornidazole, (S)-ornidazole, and (rac)-ornidazole, (e.g. in either an oral or vaginal formulation), in combination with antifungal drugs active against *Candida albicans* (including, but not limited to fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin) for the treatment of trichomoniasis or infections which are suspected to be due at least in part to trichomoniasis. The antifungal drug may be in the form of a vaginal topical or systemic (e.g. oral) formulation. A single dose treatment with an oral sachet formulation of (R)-ornidazole, (S)-ornidazole, and (rac)-ornidazole may be the only administration of (R)-ornidazole, (S)-ornidazole, and (rac)-ornidazole for the entire treatment.

If present, the single dose treatment oral sachet formulation and the vaginal topical or systemic (e.g. oral) formulation of the antifungal drug may be provided in the form of a kit.

This treatment is for strains of the causative bacterial pathogens that are both sensitive and resistant to other antibacterial agents. In many cases the protozoal infection is either mixed with other bacterial or fungal infections or these infections induce each other by altering the normal flora of the vagina. The present invention can allow more convenient empiric treatment as well as treatment when the presence of both fungal and protozoal pathogens has been demonstrated. This can prevent secondary super-infections, reduce morbidity and medical expense, and speed recovery.

The fixed doses combinations will provide the drugs with necessary spectrum of activity to eradicate common causative bacterial, protozoal and fungal pathogens together for concurrent treatment and also will have formulations appropriate to treatment at either the vaginal site of infection, systemic infection, or both.

Treatment of Bacterial Vaginosis Induced Yeast Infections

Yeast infections, also known as vaginal candidiasis, are fungal infections of the vagina. They are most commonly due to the fungus *Candida albicans*. *Candida albicans* is a common type of fungus. It is often present in small amounts in the vagina, mouth, digestive tract, and on the skin. Usually it does not cause disease or symptoms. In general, *Candida* and the many other germs or microorganisms that normally live in the vagina keep each other in balance. However, when the vagina has certain favorable conditions, the number of *Candida albicans* increases, leading to a yeast infection.

One these favorable conditions include a change the normal balance between organisms in the vagina by decreasing the number of protective bacteria like *Lactobacilli*. This often occurs in a situation of bacterial vaginosis. Hence, bacterial vaginosis, by reducing the presence of lactic acid producing *Lactobacilli* and the breakdown of the vaginal mucosal barrier by other overgrowing bacterial species such as *Bacteroides* species and *Gardnerella* species, predisposes these women to getting Vaginal candidiasis infections which often alternate with bacterial vaginosis infections and their treatment. If the underlying cause of the fungal infection is a bacterial infection that creates a suitable environment for *Candida* overgrowth, then treatment of bacterial vaginosis with an effective antibacterial agent will also prevent the establishment of yeast infections. Treatment with a combination of an antibiotic and an antifungal drug effective against *Candida albicans* will both treat existing infections and will prevent new infections by allowing the re-establishment of the natural predominant *Lactobacilli* flora.

In one group of embodiments, the present invention provides the use of (R)-ornidazole, (S)-ornidazole, and (rac)-ornidazole, (e.g. in either an oral or vaginal formulation), in combination with antifungal drugs active against *Candida albicans* (including, but not limited to fluconazole, miconazole nitrate, clotrimazole, econazole, saperconazole, terconazole, fenticonazole, sertaconazole, posaconazole, itraconazole, ketoconazole, butaconazole, tioconazole, cyclopirox, caspofungin, micafungin, and anidulafungin) for the treatment of bacterial vaginosis related and induced vaginal yeast infections. The antifungal drug may be in the form of a vaginal topical or systemic (e.g. oral) formulation. A single dose treatment with an oral sachet formulation of (R)-ornidazole, (S)-ornidazole, and (rac)-ornidazole may be the only administration of (R)-ornidazole, (S)-ornidazole, and (rac)-ornidazole during the entire treatment.

If present, the single dose treatment oral sachet formulation and the vaginal topical or systemic (e.g. oral) formulation of the antifungal drug may be provided in the form of a kit.

This treatment is for strains of the causative bacterial pathogens that are both sensitive and resistant to other antibacterial agents.

The present invention can allow more convenient empiric treatment as well as treatment when the presence of both fungal and bacterial pathogens has been demonstrated. This can prevent secondary super-infections, reduce morbidity and medical expense, and speed recovery. The combination drugs provide therapy with necessary spectrum of activity to eradicate common causative bacterial and fungal pathogens together for concurrent treatment and also will have formulations appropriate to treatment at either the vaginal site of infection, systemic infection, or both.

Treatment of Odontogenic, Dental and Periodontal Infections

In one group of embodiments, the present invention provides therapeutic uses of (R)-ornidazole, (S)-ornidazole, and (rac)-ornidazole in a combination product (e.g. a fixed dose combination product) with a macrolide (including, but not limited to erythromycin, clarithromycin, & azithromycin) antibiotic for the use of the treatment and/or prophylaxis of odontogenic, dental and periodontal infections, including, but not limited to dental carries, peri-apical abscess, periodontal abscess, and acute peri-coronitis of impacted or partially erupted teeth.

In another group of embodiments, are provided formulations (e.g. oral or parenteral formulations) comprising (R)-ornidazole, (S)-ornidazole, and (rac)-ornidazole, alone or in combination with other antibiotics in the quinolone, beta lactam, and macrolide classes, for use in treating odontogenic, dental and periodontal infections, including, but not limited to dental carries, peri-apical abscess, periodontal abscess, and acute peri-coronitis of impacted or partially erupted teeth.

In yet another group of embodiments, is provided the use of (R)-ornidazole, (S)-ornidazole, and (rac)-ornidazole in a combination product (e.g. a fixed dose combination product) with a beta lactam antibiotic for the prophylaxis and treatment of odontogenic, dental and periodontal infections, including, but not limited to dental carries, peri-apical abscess, periodontal abscess, and acute peri-coronitis of impacted or partially erupted teeth.

(R)-ornidazole, (S)-ornidazole, and (rac)-ornidazole are highly active against bacterial species including but not limited to *Bacteroides fragilis, Fusobacterium* species, *Peptostreptococcus* species, *Prevotella* species, *Pophyromonas* species, and *Actinomyces* species, the gram negative bacteria which cause clinically relevant cases of dental and periodontal infections and other antibiotic agents are active against other causative species of bacteria in these infections.

(R)-ornidazole, (S)-ornidazole, and (rac)-ornidazole are highly active against bacterial species including but not limited to biofilms of *Bacteroides fragilis, Fusobacterium* species, *Peptostreptococcus* species, *Prevotella* species, *Pophyromonas* species, and *Actinomyces* species, the gram negative bacteria which cause clinically relevant cases of dental and periodontal infections and other antibiotic agents are active against other causative species of bacteria in these infections.

In addition, the pharmacologic parameters of (R)-ornidazole, (S)-ornidazole, and (rac)-ornidazole make them appropriate to use in the setting of the treatment the above enumerated dental and periodontal gram negative bacterial infections and their related indications. (R)-ornidazole, (S)-ornidazole, and (rac)-ornidazole are rapidly absorbed after oral administration and has a longer terminal elimination half-life (approximately 14-18 hours) than commonly used drugs in the imidazole class. (R)-ornidazole, (S)-ornidazole, and (rac)-ornidazole have an improved elimination half life that enables more convenient dosing of oral formulations for these above enumerated gram negative bacterial infections including sachet formulations of powder and or pelletized granules, capsules containing (R)-ornidazole, (S)-ornidazole, and (rac)-ornidazole, oral solid tablet formulations, and liquid oral suspension formulations. These include sachet formulations with vehicles for varying absorbencies for delivery to different locations in the gastro-intestinal (GI) tract, capsules containing powders or pelletized granules with these properties, and oral solid tablet formulations with different types of slow release properties. In many of the most severe cases, parenteral formulations, such as (R)-ornidazole, (S)-ornidazole, and (rac)-ornidazole in hydrochloride form, are most appropriate for patients in these certain clinical situations where oral formulation delivery is not feasible or advisable. The disposition of (R)-ornidazole, (S)-ornidazole, and (rac)-ornidazole in the human body is similar for both oral and intravenous dosage forms and the present invention applies to the usage of both of these forms in these settings.

Summary of Organisms Against Which (R)-Ornidazole, (S)-Ornidazole, and (rac)-Ornidazole Have Activity and Indications Which They are Effective at Treating (R)-ornidazole, (S)-ornidazole, and (rac)-ornidazole may be used in the treatment of the following infections caused by both biofilms and planktonic forms of susceptible isolates of anaerobic bacteria, Gram-negative bacteria and protozoa: genitourinary infections (including but not limited to vaginitis, trichomoniasis, urethritis, sexually transmitted urethritis, urinary tract infections, pyelonephritis, prostatitis, urosepsis, cystitis, Giardiasis), gastrointestinal and/or intra-abdominal infections (including but not limited to diverticulitis, psuedomembranous colitis, gastroenteritis, infectious/*Clostridium difficile*-associated diarrhea, cholangitis, cholecystitis, pancreatitis, peptic ulcer/bleeding, peritonitis, intra-abdominal/bowel/pelvic abscess), acute bacterial skin and skin structure infections (including but not limited to cellulitis, wound infections, roseacea, Lyme Disease, diabetic foot/leg ulcers, abscesses/boils/cysts, burns, gangrene), periodontal and dental infections, lower respiratory infections (including but not limited to nosocomial pneumonia, community-acquired pneumonia, bronchitis), systemic and cardiovascular infections (including but not limited to septicemia, septic shock, bacteremia, endocarditis, indwelling catheter or device infections), bone and joint infections (including but not limited to osteomyelitis, joint infection, septic arthritis), CNS infections (including but not limited to meningitis, encephalitis, brain abscess), and upper respiratory infections (including but not limited to sinusitis, tonsillitis).

Table 1 gives a summary of various bacterial organisms and in which clinical sites they are observed.

TABLE 1

| Organism | Clinical sites of infection | | | | | |
|---|---|---|---|---|---|---|
| | BV | Oral | Respiratory | Soft tissue | Pelvic | Intra-abdominal |
| Gram-negative organisms | | | | | | |
| *Bacteroides fragilis* | | | + | +++ | ++ | +++ |
| *Bacteroides thetaiotaomicron* | | | | ++ | | +++ |
| *Parabacteroides distasonis* | | | | ++ | | +++ |

TABLE 1-continued

| Organism | BV | Oral | Respiratory | Soft tissue | Pelvic | Intra-abdominal |
|---|---|---|---|---|---|---|
| *Fusobacterium gonidiaformans* | + | | | | ++ | |
| *Fusobacterium necrophorum* | + | + | +++ | ++ | + | ++ |
| *Fusobacterium nucleatum* | + | ++ | +++ | ++ | + | ++ |
| *Porphyromonas asaccharolytica* | ++ | | | ++ | | ++ |
| *Porphyromonas gingivalis* | + | +++ | + | | + | + |
| *Porphyromonas uenonis* | + | | | | ++ | |
| *Prevotella amnii* | +++ | | | | +++ | |
| *Prevotella bivia* | +++ | | | + | +++ | + |
| *Prevotella disiens* | +++ | | | | +++ | |
| *Prevotella melaninogenica* | +++ | + | ++ | ++ | +++ | |
| *Prevotella timonensis* | +++ | | | + | +++ | |
| *Megasphaera* 1&2 | +++ | | | | | |
| Gram-positive organisms | | | | | | |
| *Gardnerella vaginalis* | +++ | | | | | |
| *Mobiluncus curtisii* | +++ | | | | | |
| *Mobiluncus mulieris* | +++ | | | | | |
| *Actinomyces israelii* | + | + | + | | + | |
| *Actinomyces neuii* ssp *neuii* | + | + | | + | + | + |
| *Actinomyces odontolyticus* | + | ++ | + | ++ | + | + |
| *Actinomyces radingae* | + | ++ | + | + | + | + |
| *Actinomyces turicensis* | + | ++ | + | ++ | ++ | ++ |
| *Peptostreptococcus anaerobius* | + | | | | ++ | ++ |
| *Peptoniphilus harei* | +++ | | | + | | |
| *Peptoniphilus asaccharolyticus* | +++ | | | + | | |
| *Peptoniphilus lacrimalis* | +++ | | | + | + | + |
| *Anaerococcus tetradius* | +++ | | | | + | |
| *Anaerococcus prevotii* | +++ | | | | + | |
| *Finegoldia magna* | + | | | +++ | | |
| *Atopobium vaginae* | +++ | | | | | |

+ infrequent;
++ sometimes;
+++ frequently (R)-Ornidazole and (S)-Ornidazole

The biological activity of the (R) and (S) enantiomer of Ornidazole may be also enhanced against resistant strains of some of the organisms which cause the infections described in this specification. The present invention of using this compound in these settings therefore provides a meaningful clinical benefit to patients through their eradication.

Additionally, the (R) and (S) enantiomers of Ornidazole in the present invention have a favorable hERG profile compared to the racemic mixture as demonstrated in the hERG assay and thus may have a higher margin of safety.

Finally, the (R) and (S) enantiomers of Ornidazole in the present invention has a diminished effect on prothrombin time and thus may have a reduced bleeding risk relative to the Ornidazole racemic mixture when combined with certain drugs effecting bleeding, like Warfarin.

The present invention of the (R) and (S) enantiomers of Ornidazole also provides a process by which the (R) and (S) enantiomers of Ornidazole can separately be synthesized specifically for therapeutic compositions as well as a method by which the racemic mixture can be separated into both the (R) and (S) stereo-isomers by a process like synthesis from 2-methyl-4-nitro-1H-imidazole by protection with chloromethyl acetate to give 1-acetoxymethyl-2-methyl-4-nitroimidazole(3), reacted with chiral cyclic sulfate followed by hydrolysis.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings, such as attached FIG. 1 Syntheses), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A method for the treatment or prophylaxis of a disease in a human or other animal associated with a dysbiosis of a microbial microbiome with bacteria in various morphological conformations, including biofilms, wherein the disease is glanders or melioidosis infections, the method comprising administering to the human or other animal in need thereof a therapeutically effective amount of (R)-ornidazole, (S)-ornidazole, a racemic mixture thereof, a pharmaceutically acceptable salt of any thereof, or an ester of any thereof.

2. The method of claim 1, wherein the glanders or melioidosis infections are caused by biofilms of *Burkholderia mallei* or *Burkholderia pseudomallei* and at least some of the bacteria are present in an anaerobic conformation.

3. The method of claim 1, wherein the ornidazole compounds are further administered in combination with one or more antibiotics, the antibiotics being selected from β-lactam antibiotics, tetracycline antibiotics, penem antibiotics, quinolone antibiotics and macrolide antibiotics.

4. The method according to claim 1 for the treatment or prophylaxis of the disease in a human.

5. The method according to claim 1 wherein at least some of the bacteria are present in an anaerobic conformation.

6. The method according to claim 1 wherein the (R)-ornidazole or the (S)-ornidazole has an enantiomeric purity selected from the group consisting of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), at least about 95% enantiomeric excess (ee), at least about 96% enantiomeric excess (ee), at least about 97% enantiomeric excess (ee), at least about 98% enantiomeric excess (ee), or at least about 99% enantiomeric excess (ee).

7. The method according to claim 1 wherein the (R)-ornidazole or the (S)-ornidazole has an enantiomeric purity of about 50% enantiomeric excess (ee) or greater.

* * * * *